United States Patent
Goto et al.

(10) Patent No.: US 7,653,224 B2
(45) Date of Patent: Jan. 26, 2010

(54) IMAGE RECONSTRUCTION METHOD AND TOMOGRAPH

(75) Inventors: Taiga Goto, Kashiwa (JP); Osamu Miyazaki, Moriya (JP); Koichi Hirokawa, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 688 days.

(21) Appl. No.: 10/588,257

(22) PCT Filed: Feb. 15, 2005

(86) PCT No.: PCT/JP2005/002264

§ 371 (c)(1),
(2), (4) Date: Jul. 31, 2006

(87) PCT Pub. No.: WO2005/077278

PCT Pub. Date: Aug. 25, 2005

(65) Prior Publication Data

US 2008/0273778 A1  Nov. 6, 2008

(30) Foreign Application Priority Data

Feb. 16, 2004 (JP) ............................. 2004-038833

(51) Int. Cl.
 *G06K 9/00* (2006.01)
(52) U.S. Cl. .................. 382/128; 382/131; 382/132
(58) Field of Classification Search .............. 382/128, 382/131, 132; 128/922; 378/14, 15, 901; 702/85
See application file for complete search history.

(56) References Cited

U.S. PATENT DOCUMENTS

| 4,549,265 A | * | 10/1985 | Deckers et al. .............. 378/14 |
| 4,580,219 A | | 4/1986 | Pelc et al. |
| 5,606,585 A | * | 2/1997 | Hu ............................. 378/15 |
| 5,668,845 A | | 9/1997 | Migita |
| 6,542,570 B1 | | 4/2003 | Silver |

FOREIGN PATENT DOCUMENTS

| JP | 60-5127 A | 1/1985 |
| JP | 8-280664 A | 10/1996 |
| JP | 2001-299738 A | 10/2001 |
| JP | 2002-78702 A | 3/2002 |

* cited by examiner

*Primary Examiner*—Tom Y Lu
(74) *Attorney, Agent, or Firm*—Cooper & Dunham, LLP

(57) ABSTRACT

A weighting function is created according to an arbitrary bio-movement correction range and a projection data angle for back-projection (width in the view direction used for reconstruction), set by a user, by considering the degree of the bio-movement and redundancy. By using this weighting function, an image reconstruction is performed.

The bio-movement correction range is set as a correction angle width index ε expressing the width guaranteed as a slope portion of the weighting function. The projection data angle for back-projection (data width) is determined by considering the data redundancy, SN, time width (time resolution) contributing to the image.

By determining the weight according to these two parameters, it is possible to apply reconstruction of projection data of all the scan ranges in the reconstruction of the tomogram and prevent lowering of the data contribution ratio as well as reduce the motion artifact, thereby obtaining a high-quality image.

21 Claims, 18 Drawing Sheets

(a)

(b)

(a)

(b)

(a)

SINGLE-ARRAY DETECTOR TYPE CT (b)

MULTI-ARRAY DETECTOR TYPE CT (a)

(b)

(a) ε=0.2 F=0.9

(b) ε=0.2 F=1.0

(c) ε=0.2 F=1.1

(a)
ε = 0.8
F = 0.9

(b)
ε = 0.8
F = 1.0

(c)
ε = 0.8
F = 1.1

(a)

(b)

(a) ε=0.0    (b) ε=0.2    (c) ε=0.4    (d) ε=0.6

(a)

F=0.8    F=0.9    F=1.0    F=1.1

(b)

F=0.8    F=0.9    F=1.0    F=1.1

(a)

(b)

(c)

TABLE FEEDING SPEED

REVOLVING AXIS z

MEASURE TWICE WITH THE SAME PHASE

TABLE FEEDING SPEED

REVOLVING AXIS z

MEASURE THREE TIMES WITH THE SAME PHASE (a) IMAGING START TIME ($\beta = 0$)

(b) IMAGING END TIME ($\beta = 2\pi$)

(c) RECONSTRUCTED IMAGE

IMAGE RECONSTRUCTION METHOD AND TOMOGRAPH

TECHNICAL FIELD

The present invention relates to a method for reconstructing a tomogram from a projection data in a computerized tomograph (hereinafter referred to as CT apparatus) using a fan beam or cone beam, more particularly to a method to reconstruct a tomogram from projection data having more than π [rad] of projection data angle using for back-projection and a CT apparatus to achieve the objective of the method thereof.

BACKGROUND ART

An X-ray CT apparatus acquires projection data by receiving an X-ray radiated from an X-ray source and transmitted through an object being examined, with an X-ray detector disposed on the opposite side of the X-ray source interposing the object therebetween. Upon acquiring the projection data, the X-ray source and the X-ray detector disposed to be opposite to each other interposing the object therebetween are revolved around revolving axis, and the projection data in different angles of rotation (phase) are collected. By reconstructing this projection data, the creation of the internal image of the object is attained in a non-destructive manner.

Such X-ray CT apparatuses are one of two kinds. One uses a single-array detector of which the detector elements are arranged one-dimensionally (line), and another kind uses a multi-array detector of which the detector elements are arranged two-dimensionally.

An imaging method in the simplest X-ray CT apparatus is the normal scanning method for creating an image by revolving an X-ray source and a detector around a revolving axis in a range of 2π, and the scanning range of the projection data acquired by this normal scanning method is 2π [rad].

On the other hand, since the above-mentioned fan beam or cone beam diverges centering around a central beam directed toward the revolving axis from the X-ray source, with regard to one beam directed toward the detector from the X-ray source, the same projection data (line integral) is measured twice during one revolution of the X-ray source and detector. Since such redundancy of data should be minimized to reduce the X-ray exposure, the imaging method for setting the scanning range at less than 2π is also adopted. As shown in FIGS. 14 (a) and (b), the beams are equivalent when the position of the X-ray source and the position of one detector element are switched, and by setting the maximum fan angle of the fan beam as 2γm as shown in FIG. 14 (c), the projection data of all beams necessary for the image reconstruction can be measured at the point of the X-ray source moving by π+2γm. This range is the minimum scanning range.

However if the image reconstruction as in the case of scanning range is 2π is carried out corresponding to the projection data obtainable from π+2γm scanning range, the image gets distorted and the image quality deteriorates. This is due to the phase range of data possible to perform back projection being different with respect to each pixel. In other words, for example, as shown in FIG. 15, in pixel p1 the data by which the phase range is more than π is used for the image reconstruction centering around pixel p1, but in pixel p2 only the data by which the phase range is less than π is used centering around pixel p2.

This means that the redundancy of the projection data is different depending on the pixel. This is illustrated in a sinogram in FIG. 16 to indicate projection data, by representing the fan angle (an angle formed by the central beam and the respective beams) γ on the horizontal axis and the revolving phase angle β on the vertical axis. In other words, FIG. 16 is a sinogram showing a minimum complete data set, and the upper and lower triangle portions denoted with diagonal lines are the data being redundant to each other.

As a method to solve the problem relating to the redundant data as mentioned above, it is suggested in Patent Document 1 to assign weight to, for example, a predetermined region of the projection data.

Patent Document: JP-A-2001-299738

With regard to weighting function w for the fan beam it generally is required to fulfill formula (1), and to fulfill formula (2) regarding weighting function w for the parallel beam.

[Formulas 1]

$$\sum_{n=0}^{\infty} \{w(\beta + 2\pi n, \gamma) + w(\pi + \beta + 2\gamma + 2\pi n, -\gamma)\} = 1 \quad (1)$$

$$\sum_{n=0}^{\infty} \{w(\beta + 2\pi n) + w(\pi + \beta + 2\pi n)\} = 1 \quad (2)$$

However, while these weighting functions can be applied to the image reconstruction from a minimum complete data set (π+2γm of scanning range) or the full-scanning data set (2π of scanning range), they are not applicable to the image reconstruction from a data set in which the scanning range is between these ranges. To solve this problem, a weighting function to be applied to data sets of intermediate-range is suggested in Patent Document 1. Here, as shown in FIG. 17, by setting and using virtual fan angle Γ which is not dependent on the actual and physical maximum fan angle, the reconstruction from the projection data with a scanning range of π+2γm~2π is achieved.

However, these weighting functions suggested in the past are not applicable to the scanning range of over 2π. Since the weighting function to apply for the scanning range changes to a different one at the point of the scanning range being over 2π, the image quality such as noise quantity or artifact intensity will also be different between the result of the reconstruction from the range narrower than 2π and the result of reconstruction from the range wider than 2π.

Also, on the virtual sinogram shown in FIG. 17, in the case that the different weight is assigned to the two triangles in the revolving phase direction, the configuration of the weighting function turns out to be a trapezium, triangle or the deformed non-linear shapes thereof, and the configuration gets closer to a triangle from a trapezium as the scanning range draws closer to 2π. This means that the region of which the weighting factor is less than 1 increases as the scanning range gets closer to 2π, and the data contribution ratio decreases significantly compared to the case that the scanning range is 2π and the weighting factor of all the range thereof is 1, which can lead to a notable increase of noise (i.e. a decrease of SNR).

Another common problem is that the imaging noise decreases as the imaging data amount to be used for the reconstruction processing increases. In other words, the imaging noise decreases as the projection data width (projection data angle using for back-projection) increases. However, acquiring a wide phase range means the redundant imaging of the same place as shown in FIG. 18, which accompanies the decrease of the measurement through-put (spiral pitch, beam pitch and table feeding speed). In this way, the decrease of the image noise and the reduction of imaging time are in trade-off relationship to each other, and the relationship between them can be inappropriate depending on the imaging purposes.

On the other hand, in order to reduce the contradiction of data by motion movement and the deterioration of image quality caused by it, the arithmetic addition of the same data is performed. More specifically, for example in normal scanning, if there is no movement of the object being examined during one revolution of the X-ray source and detector, the projection data of imaging start-time phase ($\beta$=0) coincides with the projection data of imaging end-time phase ($\beta$=2$\pi$). However, since it is impossible to completely remove the motions such as heart beats or blood flow, as shown in FIG. 19 (a)~(c) a discontinuity (data inconsistency) is generated in both projection data 51 and 52 which leads to a notable deterioration of image quantity such as streak artifacts 53 and 54. This discontinuity can be reduced by acquiring the identical data of imaging start time and imaging end time, and performing weighted addition between them. However, the assignment of a small weight causes a decrease of data contribution rate that leads to a decrease of SNR. In this way, the amount of image noise and corrective effect of discontinuity are in a trade-off relationship, and this relationship can be inappropriate in some situations.

DISCLOSURE OF THE INVENTION

Problems

As described above, with a conventional tomograph presents a difficulty to achieve the reconstruction in the projection data angle using for back-projection and also the problem that the discontinuity of the image is generated when the projection data angle using for back-projection is more than 2$\pi$. It is also difficult to perform the correction of redundancy on the imaging data without a complicated procedure. A further problem with the conventional tomograph is the deterioration of image quality by discontinuity due to the movement of the object being examined, and the difficulty in adjusting the trade-off relationship between reducing the amount of image noise and shortening the imaging time.

The present invention was implemented in order to solve various problems that the above-mentioned conventional tomogram reconstruction method have, and its objective is to provide a reconstruction method using the weighting function applicable to the reconstruction of the projection data in the entire scanning range which enables the prevention of the lowering of the data contribution ratio and the acquisition of images with good SNR, and to reduce artifacts caused by the bio-movement.

Means to Solve the Problems

In order to achieve the above-mentioned objectives, the present invention provides an image reconstruction method by creating a weighting function based on an arbitrary correction angle width (movement correction range) and projection data angle using for back-projection (width in the view direction to use for the reconstruction) taking a degree of bio-movement or redundancy into consideration, by using this weighting function.

The image reconstruction method of the present invention comprises as follows.

A tomogram reconstruction method which revolves the radiation source and the detector disposed to be opposite to each other interposing a scanning object therebetween centering on a predetermined revolving axis, detects the penetrated radiation from the radiation source which filtered out the object being radiated, and creates a tomogram of the region of interest of the object from the detected projection data, including:

a step for obtaining a weighting factor in compliance with the correction angle width and the projection data angle using for back-projection of the projection data;

a step for obtaining the projection data to which the weight is assigned by carrying out the weighting process based on the weighting factor corresponding to said projection data; and a step for reconstructing the tomogram using the weighted projection data.

The reconstruction method of the present invention can further include:

a step for setting at least one of the following, a correction angle width and/or a projection data angle using for back-projection; and a step for setting the value of either the correction angle width or the projection data angle using for back-projection which was not set in the previous setting step, based on the value of the other one being set in the previous step.

The correction angle width and the projection data angle using for back-projection are set, for example, as $0 \leq \epsilon \leq (2F-1)$ (only $\epsilon \neq 2F-2^{ceil(log 2F)}$) when the correction angle width is set as $\epsilon \pi$ and the projection data angle using for back-projection as 2F. Hereinafter $\epsilon$ is referred to as the correction angle width index and F as the index of projection data angle using for back-projection.

The correction angle width is for eliminating the discontinuity due to motion movement being generated between a set of projection data and the following projection data to be measured and also for correcting data redundancy. The correction angle width index $\epsilon$ is for representing the minimum guaranteed width of the slope portion of the weighting function. The correction angle width is set corresponding to the range of the region for correcting the data discontinuity (hereinafter referred to as the data discontinuity region) in, for example, the end portion of the projection data. Or, the correction angle width may be changed according to the amount of noise or motion artifact in reconstructed images. The correction angle width can also be increased or decreased by making it directly proportional to the projection data angle using for back-projection.

The projection data angle using for back-projection (data width) is determined considering the time-width (time resolution) contributing to the data redundancy, SN, and images. It can also be set at any angle that is greater than data width of a minimum complete data set [two-times the value of the maximum of $\pi$+fan angle].

The weighting function being created based on the correction angle width index $\epsilon$ and index F of projection data angle using for back-projection is set so that the weight of the data discontinuity region (weighting factor) turns out smaller than the weight of other region that is equivalent to said data discontinuity. For example, the second sub weighting function and the second sub weighting function being created by shifting the second sub weighting function by a predetermined phase can be added and normalized.

To be more precise, it is obtained by:

(1) First obtaining one weighting function (a first sub weighting function) which has the same size redundancy correcting region as the set bio-movement correcting range, which satisfies the previously mentioned formula (1) or (2);

(2) making the weighting function which has the same form as the above-mentioned weighting function as a second sub weighting function by shifting it for a predetermined phase being determined by the scanning range; and (3) performing addition on the first sub weighting function and the second sub weighting function, and normalizing it (performing the multiplication on the gain for sub-weight function).

As an example of the sub weighting function, a shape of trapezium with $\pi-\epsilon\pi$ as an upper hem and $\pi+\epsilon\pi$ as a bottom can be cited.

The projection data applying the weighting function obtained in this way has no distortion of images caused by redundancy, due to the discontinuity among data being corrected according to the demand of users indicated with the correction angle width index. Also if the scanning range is more than $\pi$, it can be applied to the projection data with any projection data angle using for back-projection whether it is less than $2\pi$ or more than $2\pi$, so the problem with the discontinuity of which existed at $2\pi$ of scanning range is solved.

Also, the reconstruction method for the tomogram in the present invention further includes a step for implementing the process to rearrange the fan beam radiated from the radiation source to the parallel beam, and the weighting functions $w(\theta)$ when the revolving phase (view phase) at the time of detecting the projection data is set as $\theta$ and using N which can be obtained from the correction angle width $\epsilon\pi$ [rad] and $2^{(N-1)} \leq F-\epsilon/2 < 2^N$ (N is an integer of more than 0) are:

$w(\theta)=0$ if $[\theta < P_0\pi]$ $w(\theta)=(P_7\pi+\theta)W1/(\epsilon\pi)$ if $[P_0\pi \leq \theta < P_1\pi, \epsilon>0]$ $w(\theta)=0$ if $[P_0\pi \leq \theta < P_1\pi, \epsilon=0]$ $w(\theta)=W1*V2*2/\epsilon$ if $[P_1\pi \leq \theta < P_2\pi, \epsilon>0, V1=0]$ $w(\theta)=((\theta-P_1\pi)*(W1*4/\epsilon)/2\pi)+W1*V2*2/\epsilon$ if $[P_1\pi \leq \theta < P_2\pi, \epsilon>0, V1\neq 0]$ $w(\theta)=W1$ if $[P_1\pi \leq \theta < P_2\pi, \epsilon=0]$ $w(\theta)=((\theta-P_3\pi)*W1/(\epsilon\pi))+W2$ if $[P_2\pi \leq \theta < P_3\pi, \epsilon>0]$ $w(\theta)=W2$ if $[P_3\pi \leq \theta < P_4\pi]$ $w(\theta)=((P_4\pi-\theta)*W1/(\epsilon\pi))+W2$ if $[P_4\pi \leq \theta < P_5\pi, \epsilon>0]$ $w(\theta)=W1*V2*2/\epsilon$ if $[P_5\pi \leq \theta < P_6\pi, \epsilon>0, V1=0]$ $w(\theta)=((P6\pi-\theta)*(W1*4/\epsilon)/2\pi)+W1*V2*2/\epsilon$ if $[P_5\pi \leq \theta < P_6\pi, \epsilon>0, V1\neq 0]$ $w(\theta)=W1$ if $[P_5\pi \leq \theta < P_6\pi, \epsilon=0]$ $w(\theta)=(P_7\pi-\theta)W1/(\epsilon\pi)$ if $[P_6\pi \leq \theta < P_7\pi, \epsilon>0]$ $w(\theta)=0$ if $[P_6\pi \leq \theta < P_7\pi, \epsilon=0]$ $w(\theta)=0$ [Formula 2A]

if $[P_7\pi \leq \theta]$.

Here, the respective parameters in the above formulas are determined by the following respective formulas:

$V1=\epsilon-F+2^{(N-1)}$ if $[\epsilon-F+2^{(N-1)}>0]$ $V2=\epsilon/2-V1$ $M=2^N$ $W1=1/2^N$ $W2=1/2^{(N-1)}$ if $[\epsilon \leq 0]$ $W2=2*W1$ if $[\epsilon>0, F<M]$ $W2=(2*(M-F)+\epsilon)*W1/\epsilon+W1$ if $[\epsilon>0, M \leq F]$ $AA=-F$ $BB=-F+\epsilon$ $CC=M-F$ $DD=M-F+\epsilon$ $EE=F-M-\epsilon$ $FF=F-M$ $GG=F-\epsilon$ $HH=F$ $Po=AA$ $P_1=BB$ if $[F<M/2+\epsilon/2]$ $P_1=EE$ if $[M/2+\epsilon/2 \leq F<M/2+\epsilon]$ $P_1=BB$ if $[M/2+\epsilon \leq F]$ $P_2=BB$ if $[M/2+\epsilon/2 \leq F<M/2+\epsilon]$ $P_2=EE$ if $[M/2+\epsilon \leq F<M+\epsilon/2]$ $P_2=CC$ if $[M+\epsilon/2 \leq F]$ $P_3=FF$ if $[M/2+\epsilon/2 \leq F<M]$ $P_3=CC$ if $[M \leq F<M+\epsilon/2]$ $P_3=EE$ if $[M+\epsilon/2 \leq F]$ $P_4=CC$ if $[M/2+\epsilon/2 \leq F<M]$ $P_4=FF$ if $[M \leq F<M+\epsilon/2]$ $P_4=DD$ if $[M+\epsilon/2 \leq F]$ $P_5=GG$ if $[M/2+\epsilon/2 \leq F<M/2+\epsilon]$ $P_5=DD$ if $[M/2+\epsilon \leq F<M+\epsilon/2]$ $P_5=FF$ if $[M+\epsilon/2 \leq F]$ $P_6=GG$ if $[F<M/2+\epsilon/2]$ $P_6=DD$ if $[M/2+\epsilon/2 \leq F<M/2+\epsilon]$ $P_6=GG$ if $[M/2+\epsilon \leq F]$ $P_7=HH$. [Formula 2B]

The above-mentioned weighting functions can be expressed with formula (3) using the following formulas (4)~(8):

[Formulas 3]

$$Wp(\theta) = G \cdot \left\{ Ws\left(\frac{\theta}{2\pi} - \theta_{c1}, \eta, \varepsilon\right) + Ws\left(\frac{\theta}{2\pi} - \theta_{c2}, \eta, \varepsilon\right) \right\} \quad (3)$$

$$Ws(\xi, \eta, \varepsilon) = \begin{cases} 0 & \text{if } |\xi| \geq \frac{(\eta + \varepsilon/2)}{2} \\ 1 & \text{if } |\xi| \geq \frac{(\eta - \varepsilon/2)}{2} \\ \frac{1}{\varepsilon/2} \cdot \left(\frac{\eta + \varepsilon/2}{2} - |\theta|\right) & \text{otherwise,} \end{cases} \quad (4)$$

$$\theta_{c1} = -\frac{2\eta + \varepsilon - F}{2} \quad (5)$$

$$\theta_{c2} = \frac{2\eta + \varepsilon - F}{2} \quad (6)$$

$$\eta = 2^{N-1} \quad (7)$$

$$G = 2^{-N}. \quad (8)$$

Here, $W_S$ is the sub weight for the parallel beam, $\theta$ is the view phase, $\theta_{c1}$ and $\theta_{c2}$ are the central view phase of the sub weight, $\eta$ is the sub weight reference width, G is the gain for sub-weight function, N is an integer of more than 0 being $2^{(N-1)} \leq F - \varepsilon/2 < 2^N$. Correction angle width index $\varepsilon$ and/or back projection width index F are inputted by the user, and the other is determined automatically.

Or, it also is possible to make formula (3) a non-linear weighting function by correcting the sub weight of it to be non-linear. The non-linear weighting function is expressed with formula (3') using the above-mentioned formulas (4)~(9).

[Formulas 4]

$$Wp(\theta) = G \cdot \left\{ NL\left(Ws\left(\frac{\theta}{2\pi} - \theta_{c1}, \eta, \varepsilon\right)\right) + NL\left(Ws\left(\frac{\theta}{2\pi} - \theta_{c2}, \eta, \varepsilon\right)\right) \right\} \quad (3')$$

$$NL(w) = 3w^2 - 2w^3 \quad (9)$$

As for a fan beam, the weighting functions w ($\theta, \gamma$) for the reconstruction of the fan beam in the case of setting the projection phase of the fan beam as $\theta$ and the fan angle as $\gamma$, using N which can be obtained from the correction angle width $\varepsilon\pi$ [rad] and $2^{(N-1)} \leq F - \varepsilon/2 < 2^N$ (N is an integer of more than 0) are:

$w(\theta)=0$ if $[\theta < P_0\pi]$ $w(\theta)=(P_7\pi+\theta)W1/(\varepsilon\pi)$ if $[P_0\pi \leq \theta < P_1\pi, \varepsilon > 0]$ $w(\theta)=0$ if $[P_0\pi \leq \theta < P_1\pi, \varepsilon = 0]$ $w(\theta)=W1*V2*2/\varepsilon$ if $[P_1\pi \leq \theta < P_2\pi, \varepsilon > 0, V1=0]$ $w(\theta)=((\theta-P_1\pi)*(W1*4/\varepsilon)/2\pi)+W1*V2*2/\varepsilon$ if $[P_1\pi \leq \theta < P_2\pi, \varepsilon > 0, V1 \neq 0]$ $w(\theta)=W1$ if $[P_1\pi \leq \theta < P_2\pi, \varepsilon = 0]$ $w(\theta)=((\theta-P_3\pi)*W1/(\varepsilon\pi))+W2$ if $[P_2\pi \leq \theta < P_3\pi, \varepsilon > 0]$ $w(\theta)=W2$ if $[P_3\pi \leq \theta < P_4\pi]$ $w(\theta)=(P_4\pi-\theta)*W1/(\varepsilon\pi))+W2$ if $[P_4\pi \leq \theta < P_5\pi, \varepsilon > 0]$ $w(\theta)=W1*V2*2/\varepsilon$ if $[P_5\pi \leq \theta < P_6\pi, \varepsilon > 0, V1=0]$ $w(\theta)=((P_6\pi-\theta)*(W1*4/\varepsilon)/2\pi)+W1*V2*2/\varepsilon$ if $[P_5\pi \leq \theta < P_6\pi, \varepsilon > 0, V1 \neq 0]$ $w(\theta)=W1$ if $[P_5\pi \leq \theta < P_6\pi, \varepsilon = 0]$ $w(\theta)=(P_7\pi-\theta)W1/(\varepsilon\pi)$ if $[P_6\pi \leq \theta < P_7\pi, \varepsilon > 0]$ $w(\theta)=0$ if $[P_6\pi \leq \theta < P_7\pi, \varepsilon = 0]$ $w(\theta)=0$ [Formula 5A]

if $[P_7\pi \leq \theta]$.

Here, the respective parameters in the above formulas are determined by the following respective formulas:

$V1=\varepsilon-F+2^{(N-1)}$ if $[\varepsilon-F+2^{(N-1)}>0]$ $V2=\varepsilon/2-V1$ $M=2^N$ $W1=1/2^N$ $W2=1/2^{(N-1)}$ if $[\varepsilon \leq 0]$ $W2=2*W1$ if $[\varepsilon>0, F<M]$ $W2=(2*(M-F)+\varepsilon)*W1/\varepsilon+W1$ if $[\varepsilon>0, M \leq F]$ $AA=-F$ $BB=-F+\varepsilon$ $CC=M-F$ $DD=M-F+\varepsilon$ $EE=F-M-\varepsilon$ $FF=F-M$ $GG=F-\varepsilon$ $HH=F$ $Po=AA$ $P_1=BB$ if $[F<M/2+\varepsilon/2]$ $P_1=EE$ if $[M/2+\varepsilon/2 \leq F<M/2+\varepsilon]$ $P_1=BB$ if $[M/2+\varepsilon \leq F]$ $P_2=BB$ if $[M/2+\varepsilon \leq F<M/2+\varepsilon]$ $P_2=EE$ if $[M/2+\varepsilon \leq F<M+\varepsilon/2]$ $P_2$=CC if [$M+\epsilon/2 \leq F$]

$P_3$=FF if [$M/2+\epsilon/2 \leq F<M$]

$P_3$=CC if [$M \leq F<M+\epsilon/2$]

$P_3$=EE if [$M+\epsilon/2 \leq F$]

$P_4$=CC if [$M/2+\epsilon/2 \leq F<M$]

$P_4$=FF if [$M \leq F<M+\epsilon/2$]

$P_4$=DD if [$M+\epsilon/2 \leq F$]

$P_5$=GG if [$M/2+\epsilon/2 \leq F<M/2+\epsilon$]

$P_5$=DD if [$M/2+\epsilon \leq F<M+\epsilon/2$]

$P_5$=FF if [$M+\epsilon/2 \leq F$]

$P_6$=GG if [$F<M/2+\epsilon/2$]

$P_6$=DD if [$M/2+\epsilon/2 \leq F<M/2+\epsilon$]

$P_6$=GG if [$M/2+\epsilon \leq F$]

$P_7$=HH.  [Formula 5B]

Weighting function $Wf(\theta, \gamma)$ in relation to the fan beam can be expressed with formula (10) by using the same presenting method as weighting function $Wp(\theta)$ regarding the above-mentioned parallel beam, and also with formula (10') using the non-linear sub weight. Either one of these may be used with regard to the fan beam.

[Formulas 6]

$$Wf(\theta, \gamma) = G \cdot \left\{ Ws\left(\frac{\theta-\gamma}{2\pi} - \theta_{c1}, \eta, \varepsilon\right) + Ws\left(\frac{\theta-\gamma}{2\pi} - \theta_{c2}, \eta, \varepsilon\right) \right\} \quad (10)$$

$$Wf(\theta, \gamma) = \quad (10')$$
$$G \cdot \left\{ NL\left(Ws\left(\frac{\theta-\gamma}{2\pi} - \theta_{c1}, \eta, \varepsilon\right)\right) + NL\left(Ws\left(\frac{\theta-\gamma}{2\pi} - \theta_{c2}, \eta, \varepsilon\right)\right) \right\}$$

Also, in the reconstruction method for tomograms in the present invention, the projection data can be data detected as an object being shifted in the revolving axis direction along with the revolution of the radiation source and the detector. In such a case, a step of interpolating the projection data and creating the projection data of the orthogonal side to the revolving axis (called "2-dimensional interval projection processing") is included.

A tomograph of the present invention includes:

a radiation source and a detector disposed to be opposite to each other interposing an object therebetween;

a reconstruction means for creating a tomographic image of the region of interest of the object from the projection data detected by the detector; and an imaging control means for controlling the radiation source, detector and reconstruction means, wherein the reconstruction means is mounted with the above-mentioned reconstruction method of tomograms.

In the tomograph of the present invention, the imaging control means can change the projection data angle using for back-projection according to the imaging region. For example, it can improve SNR for imaging by widening the projection data angle using for back-projection, or can improve the time resolution for imaging by narrowing the projection data angle using for back-projection. Also, the tomograph of the present invention is provided with a meaning for moving an object in the revolving axis direction, wherein the imaging control means can change the correction angle width and/or the projection data angle using for back-projection to use for the reconstruction according to the movement velocity of the object in the revolving axis direction.

In the tomograph of the present invention, the detector may be either a single-array detector or a multi-array detector. When it is the multi-array detector, the reconstruction means may use the same weighting factor with regard to the respective array of the detector, or may use a different weighting factor from other arrays with regard to at least one of the rows of the detector.

Moreover, the tomograph of the present invention preferably comprises an input means for accepting the information from the users relating to the correction angle width and the projection data angle using for back-projection.

ADVANTAGEOUS EFFECT OF THE INVENTION

According to the present invention, it is possible to perform a reconstruction using the weighting function which can correspond to the back projection with either fan beam or parallel beam, and is also applicable to the consecutive phase width from narrow projection data angle using for back-projection having raised contribution rate to wide projection data angle using for back-projection having data redundancy, and to attain high-definition tomograms without the problems of data discontinuity or noise.

Concretely, the weighting function in the present invention does not form a rectangle due to the minimum correction angle width being maintained by the correction angle width index $\epsilon$ being set at more than 0 ($\epsilon>0$). Taking a weighting function shape for the parallel beam for example, the conventional idea would be that the weighting function shape turns out to be a rectangle as seen in FIG. 11 (b) when index F of projection data angle using for back-projection=1.0, but with the same index F of projection data angle using for back-projection=1.0 by setting the correction angle width index $\epsilon$ at 0.2 the weighting function shape of the present invention turns out to be a two-tier trapezium as shown in FIG. 11 (a), and the weight slope is being maintained. This indicates that the influence caused by the movement can be reduced by using the weighting function of the present invention since the data discontinuity upon the phase being 0 and the phase being $2\pi$ is restrained by the data of phase $\pi$ which is the opposite data of the data discontinuity. Making the weighting function nonlinear enables the attainment of better results.

BEST MODE FOR CARRYING OUT THE INVENTION

The embodiment of the present invention will be described below referring to the attached drawings.

FIG. 1 is a diagram showing an overview of a CT apparatus for implementing the reconstruction method of to tomograms of the present invention. This CT apparatus mainly comprises scanner 40, operation unit 50, and table 60 for laying and moving an object. Scanner 40 comprises units such as central controller 400, X-ray controller 401, high-voltage generator 402, high-voltage switching unit 403, X-ray generator 404, X-ray detector 405, preamplifier 406, scanner controller 407, driver 408, collimator controller 409, table controller 410, and table-feeding measurement unit 411.

Operation unit 50 comprises input/output unit 51 including units such as the display unit, input unit and storage unit and calculation unit 52 including units such as reconstruction calculator and image processor. The input unit comprises a device such as mouse or keyboard, and is for inputting the measurement/reconstruction parameter such as the table feeding speed information or reconstruction position. In the present invention it is possible for a user to set correction angle width index $\epsilon$ and index F of projection data angle using for back-projection as a necessary parameter to obtain the weighting function to use for the image reconstruction of the projection data which is obtained additionally, and these index are also inputted from input unit. A detailed description of correction angle width index $\epsilon$ and index F of projection data angle using for back-projection will be presented later. The storage unit is for storing information being inputted from input unit or the processing results in calculation unit 52. The display unit is for displaying the various types of data such as above-mentioned information or reconstructed images. The reconstruction calculator is for processing the data obtained from the X-ray detector, and the image processor is for implementing various processing on images such as a reconstructed image and displaying them to the display unit.

Central processing controller 400 is for transmitting the necessary controlling signals for imaging to X-ray controller 401, table controller 410 and scanner controller 407 based on the imaging condition (such as table feeding speed, tube-current, tube-voltage and slice position) being inputted from the input unit of operation unit 50 or the reconstruction parameter (such as the region of interest, size of reconstructed images, projection data angle using for back-projection and reconstruction filter function), and starting the imaging upon receiving the starting-signal. Upon starting the imaging, the controlling signal is transmitted to high-voltage generator 402 by X-ray controller 401, high-voltage is applied to X-ray generator 404 via high-voltage switching unit 403, the X-ray outputted from X-ray generator 404 is irradiated to an object being examined, and the transmitted X-ray is inputted to X-ray detector 405. Simultaneously, a controlling signal is transmitted from scanner controller 407 to driver 408, and X-ray generator 404, X-ray detector 405 and preamplifier 406 are controlled to revolve around the object. When executing circular orbit scanner (normal scanning) 41 as shown in FIG. 2(*a*), table 60 where the object is laid down, comes to rest during the revolution at the command of table controller 410. Also when executing helical orbit scanning 42 as shown in FIG. 2 (*b*) the location of table 60 is shifted in the revolving axis direction of units such as X-ray generator 404 with a predetermined pitch. In the helical scanning method, when the distance of the table feeding relative to the scanner during one revolution of the scanner is set as distance Δx, the ratio of the detecting element in the revolting axis direction width D (D/Δx) is defined as the helical pitch, and the ratio of the detector to the entire length of the revolving axis direction is defined as the beam pitch. The higher these pitches are, indicates that the imaging time for the same range can be shortened and imaging performance can be improved. Generally the helical pitch is used to a degree of "2" which can cover almost the entire imaging region in consideration of the opposite data.

The X-ray outputted from X-ray generator 404 gets restricted in its irradiation area by collimator 412 under the control of collimator controller 409, transmits through the object, being absorbed (attenuated) in the respective tissues in the body of the object, and gets detected by X-ray detector 405. The X-ray being detected by X-ray detector 405 is converted into a current at that point, amplified by preamplifier 406, and inputted to calculator 52 of operation unit 50 as a projection data signal. The projection data signal inputted to calculator 52 receives the image reconstruction processing by the reconstruction calculator in calculator 52. This reconstructed image is stored in the storage unit of input/output unit 51, and displayed on the display unit as a CT image.

X-ray detector 405 may be either single-array detector 11 as shown in FIG. 3 (*a*) in which the detecting elements are arranged in one dimension, or multi-array detector 12 as shown in FIG. 3 (*b*) in which the single-array detector is arranged in a plurality of rows in the revolving axis direction (the direction of the arrow in the diagram). Additionally, while detector 11 is shown in a straight line in FIG. 3 (*a*), generally the one with the detecting elements arranged in a circular arc shape is used so that the distance from X-ray source 10 to the respective detector elements or the angle between the adjacent X-ray beams will be equal. In the single-array detector, the X-ray beam is orthogonal to the revolving axis. In the multi-array detector, a wide range can be imaged in one imaging compare to the single-array detector, but as it moves away from the mid-lane (central row) in the revolving axis direction the X-ray beam forms a tilt angle (cone angle).

The processes to be carried out in the reconstruction calculator are, for example, the rearrangement process for coordinating the fan beam projection data obtained by the fan beam with the parallel beam projection data in a parallel form, the data correction process for calculating the weighting function to apply to the fan beam projection data or parallel beam projection data and for applying the weighting function to these projection data, the filter correction process for generating the filter processing parallel beam projection data by superimposing the reconstruction filter to the parallel projection data, the back projection process for implementing the back projection of the filter processing parallel beam projection data to the back projection region relating to the region of interest, and the data interpolation process for creating the data like circular orbit by carrying out the data interpolation to the data obtained upon the helical orbit scanning. Also in the case that detector 405 is the multi-array detector as shown in FIG. 3 (*b*), the cone angle correction process for performing the multiplication on the coefficient depending on the tilt angle of the radiation relating to the respective row of projection data is carried out.

Next, the tomogram reconstruction method in the X-ray CT apparatus of the above-mentioned configuration will be described. The procedure of the reconstruction method is illustrated in FIG. 4 (*a*). The imaging method may be either one of the circular orbit scanning or the helical scanning, and the case with the circular orbit scanning will be described here.

As mentioned above, the projection data can be obtained by X-ray generator 404, X-ray detector 405 and preamplifier 406 revolving around an object while an X-ray outputted from X-ray generator 404 being irradiated to the object and the transmitted X-ray is imputed to X-ray detector 405 (step 101). The scanning range is 2Fπ being determined by index F of projection data angle using for back-projection inputted from the input unit, and in the case for the parallel beam it is more than π. In other words the numeric value that satisfies F≧0.5 as the index F of projection data angle using for back-projection is inputted. As for the circular orbit scanning, the user determines the appropriate value in consideration of the exposure quantity of the X-ray, time resolution or noise.

First, the obtained fan beam projection data is rearranged to the parallel beam projection data (step 102). This rearrangement process is the process of combining the data from different phases and fan angles from the fan beam being irradiated radially from the revolving axis direction as shown in FIG. 5 (*a*), and converting it into a parallel beam that is parallel from the revolving axis direction as shown in FIG. 5(b). S1 and S2 in FIG. 5 indicate the position of the radiation source and the detector. While the address on the detector of the X-ray beam passing through the reconstruction pixels in the respective projection phase is calculated in the back projection process that is heavily used as the reconstruction method, by using the parallel beam, the inverse trigonometric function which is time consuming and high in calculation load and the distance calculation between the X-ray source and the reconstruction pixel become unnecessary, and an inverse trigonometric function can be replaced with a product-sum operation. Therefore in spite of the increase of calculation time for the rearrangement process, it has the advantage of speeding up the time required for the reconstruction process.

Next as the data correction process, a correction is carried out for eliminating image distortion due to the bio-movement correction of the projection data or redundancy (step 103). In the data correction process, weighting function $w(\theta)$ for applying to the parallel beam is obtained based on correction angle width index $\epsilon$ and index F of projection data angle using for back-projection inputted from the input unit. Correction angle width index $\epsilon$ is set by the user for the purpose of eliminating data discontinuity by bio-movement in consideration of the degree of bio-movement in compliance with conditions such as the imaging region of the object, and is set to be $0 \leq \epsilon \leq (2F-1)$ which is the range not surpassing [scanning width $(2F\pi)-\pi$] when the correction angle width is set as $\epsilon\pi$.

The weighting function $w(\theta)$ ($\theta$ is the projection phase) satisfies the following formula (1) (in the case of a fan beam) or formula (2) (in the case of a parallel beam) with regard to the correction region of the projection data determined by correction angle width $\epsilon\pi$ as shown in FIG. 6,

[Formulas 7]

$$\sum_{n=0}^{\infty} \{w(\beta + 2\pi n, \gamma) + w(\pi + \beta + 2\gamma + 2\pi n, -\gamma)\} = 1 \quad (1)$$

$$\sum_{n=0}^{\infty} \{w(\beta + 2\pi n) + w(\pi + \beta + 2\pi n)\} = 1 \quad (2)$$

and is obtained by acquiring the sub weighting function $W_S(\theta)$ of the trapezium shape with $\pi+\epsilon\pi$ as the bottom and $\pi-\epsilon\pi$ as the upper hem, adding the function of which this sub weight function $W_S(\theta)$ being shifted to $(2F\pi-(\pi+\epsilon\pi))$ by a predetermined phase being determined by scanning width $2F\pi$ in relation to the center of data width, and implementing the normalization. Normalization is the process of making the average weight of the respective phase equal 1.

In concrete terms, it is calculated by the formulas below using N which satisfies $2^{(N-1)} \leq F-\epsilon/2 < 2^N$ (N is an integer of more than 0).

$w(\theta)=0$ if $[\theta<P_0\pi]$ $w(\theta)=(P_7\pi+\theta)W1/(\epsilon\pi)$ if $[P_0\pi \leq \theta<P_1\pi, \epsilon>0]$ $w(\theta)=0$ if $[P_0\pi \leq \theta<P_1\pi, \epsilon=0]$ $w(\theta)=W1*V2*2/\epsilon$ if $[P_1\pi \leq \theta<P_2\pi, \epsilon>0, V1=0]$ $w(\theta)=((\theta-P_1\pi)*(W1*4/\epsilon)/2\pi)+W1*V2*2/\epsilon$ if $[P_1\pi \leq \theta<P_2\pi, \epsilon>0, V1\neq 0]$ $w(\theta)=W1$ if $[P_1\pi \leq \theta<P_2\pi, \epsilon=0]$ $w(\theta)=((\theta-P_3\pi)*W1/(\epsilon\pi))+W2$ if $[P_2\pi \leq \theta<P_3\pi, \epsilon>0]$ $w(\theta)=W2$ if $[P_3\pi \leq \theta<P_4\pi]$ $w(\theta)=((P_4\pi-\theta)*W1/(\epsilon\pi))+W2$ if $[P_4\pi \leq \theta<P_5\pi, \epsilon>0]$ $w(\theta)=W1*V2*2/\epsilon$ if $[P_5\pi \leq \theta<P_6\pi, \epsilon>0, V1=0]$ $w(\theta)=((P6\pi-\theta)*(W1*4/\epsilon)/2\pi)+W1*V2*2/\epsilon$ if $[P_5\pi \leq \theta<P_6\pi, \epsilon>0, V1\neq 0]$ $w(\theta)=W1$ if $[P_5\pi \leq \theta<P_6\pi, \epsilon=0]$ $w(\theta)=(P_7\pi-\theta)W1/(\epsilon\pi)$ if $[P_6\pi \leq \theta<P_7\pi, \epsilon>0]$ $w(\theta)=0$ if $[P_6\pi \leq \theta<P_7\pi, \epsilon=0]$ $w(\theta)=0$ [Formula 8A]

if $[P_7\pi \leq \theta]$.

Here, the respective parameters in the above formulas are determined by the following respective formulas:

$V1=\epsilon-F+2^{(N-1)}$ if $[\epsilon-F+2^{(N-1)}>0]$ $V2-\epsilon/2-V1$ $M=2^N$ $W1=\frac{1}{2}^N$ $W2=\frac{1}{2}^{(N-1)}$ if $[\epsilon \leq 0]$ $W2=2*W1$ if $[\epsilon>0, F<M]$ $W2=(2*(M-F)+\epsilon)*W1/\epsilon+W1$ if $[\epsilon>0, M \leq F]$ $AA=-F$ $BB=-F+\epsilon$ $CC=M-F$ $DD=M-F+\epsilon$ $EE=F-M-\epsilon$ $FF=F-M$ $GG=F-\epsilon$ $HH=F$ $Po=AA$ $P_1=BB$ if $[F<M/2+\epsilon/2]$ $P_1=EE$ if $[M/2+\epsilon/2 \leq F<M/2+\epsilon]$ $P_1$=BB if [$M/2+\epsilon \leq F$]

$P_2$=BB if [$M/2+\epsilon/2 \leq F < M/2+\epsilon$]

$P_2$=EE if [$M/2+\epsilon \leq F < M+\epsilon/2$]

$P_2$=CC if [$M+\epsilon/2 \leq F$]

$P_3$=FF if [$M/2+\epsilon/2 \leq F < M$]

$P_3$=CC if [$M \leq F < M+\epsilon/2$]

$P_3$=EE if [$M+\epsilon/2 \leq F$]

$P_4$=CC if [$M/2+\epsilon/2 \leq F < M$]

$P_4$=FF if [$M \leq F < M+\epsilon/2$]

$P_4$=DD if [$M+\epsilon/2 \leq F$]

$P_5$=GG if [$M/2+\epsilon/2 \leq F < M/2+\epsilon$]

$P_5$=DD if [$M/2+\epsilon \leq F < M+\epsilon/2$]

$P_5$=FF if [$M+\epsilon/2 \leq F$]

$P_6$=GG if [$F < M/2+\epsilon/2$]

$P_6$=DD if [$M/2+\epsilon/2 \leq F < M/2+\epsilon$]

$P_6$=GG if [$M/2+\epsilon \leq F$]

$P_7$=HH. [Formula 8B]

This weight function Wp for the parallel beam can be expressed by formula (3) using the following formulas (4)~(8).

[Formulas 9]

$$Wp(\theta) = G \cdot \left\{ Ws\left(\frac{\theta}{2\pi} - \theta_{c1}, \eta, \varepsilon\right) + Ws\left(\frac{\theta}{2\pi} - \theta_{c2}, \eta, \varepsilon\right) \right\} \quad (3)$$

$$Ws(\xi, \eta, \varepsilon) = \begin{cases} 0 & \text{if } |\xi| \geq \frac{(\eta+\varepsilon/2)}{2} \\ 1 & \text{if } |\xi| \geq \frac{(\eta-\varepsilon/2)}{2} \\ \frac{1}{\varepsilon/2} \cdot \left(\frac{\eta+\varepsilon/2}{2} - |\theta|\right) & \text{otherwise,} \end{cases} \quad (4)$$

$$\theta_{c1} = -\frac{2\eta + \varepsilon - F}{2} \quad (5)$$

$$\theta_{c2} = \frac{2\eta + \varepsilon - F}{2} \quad (6)$$

$$\eta = 2^{N-1} \quad (7)$$

$$G = 2^{-N} \quad (8)$$

Here, $W_S$ is the sub weight for the parallel beam, $\theta$ is the view phase, $\theta_{C1}$ and $\theta_{C2}$ are the central view phase of the sub weight, $\eta$ is the sub weight reference width, G is the gain for sub-weight function, N is an integer of more than 0 to be $2^{(N-1)} \leq F-\epsilon/2 < 2^N$. Correction angle width index $\epsilon$ and/or back projection width index F is inputted by the user, and the other is determined automatically.

Or, it is also possible to correct formula (3) in such a way that the sub weight turns out to be non-linear, and make it a non-linear weighting function. In other words the non-linear weighting function can be expressed as formula (3') using the above-described formulas (4)~(8) and formula (9) described below.

[Formulas 10]

$$Wp(\theta) = G \cdot \left\{ NL\left(Ws\left(\frac{\theta}{2\pi} - \theta_{c1}, \eta, \varepsilon\right)\right) + NL\left(Ws\left(\frac{\theta}{2\pi} - \theta_{c2}, \eta, \varepsilon\right)\right) \right\} \quad (3')$$

$$NL(w) = 3w^2 - 2w^3 \quad (9)$$

In concrete terms, the weighting function in the case when the correction angle width index is $\epsilon$=0.2 and when $\epsilon$=0.8 is illustrated in FIGS. 7 and 8. In FIGS. 7 and 8, each of (a), (b) and (c) shows a case when index F projection data angle using for back-projection is 0.9, 1.0 and 1.1 respectively. As indicated in the drawings, this weighting function can be applied to the projection data of more than π and of arbitrary projection data angle using for back-projection by setting index F of projection data angle using for back-projection. Also by setting correction angle width index $\epsilon$, it is possible to obtain definite corrective effect which enables correction of the discontinuity in the end portion of the data, even in the case of the projection data angle using for back-projection having any value such as 1.3π or 2π. Furthermore, this weighting function can use the same weighting function corresponding to all the channel positions of the parallel beam (the position corresponding to the fan angle position of the fan beam), and store the weight with a small amount of memory. Also, the method according to the present embodiment can include redundant data in CT reconstruction without using the weight of which the phase width is limited. In the case of correction angle width index $\epsilon$=0, it is possible to obtain the projection image placing as much value on the reduction of noise as in the past.

Next, with regard to the parallel beam projection data applying the weighting function being obtained in this way, the reconstruction filtering process is carried out superposing the reconstruction filtering function in the channel direction (step 104), after that the back projection process is implemented and the CT image is obtained (step 105). As for the reconstruction filtering and the back projection process, heretofore known methods can be used.

While CT apparatus using a single-array detector was described in the above-mentioned embodiment, in the CT apparatus using the multi-array detector, since the projection data relating to the detection elements of the plurality of arrays placed in the revolving axis direction can be obtained, each of the above-mentioned rearrangement process (step 102) and correction process using the weighting function (step 103) are implemented corresponding to the projection data with respect to each row. Then by performing the multiplication of the cosine of the several cone angles corresponding to each row on the parallel beam projection data, carrying out the reconstruction filtering process which superimposes the reconstruction filtering function in the channel direction of the each row of parallel beam, and further implementing the 3-dimensional back projection process, CT images similar to CT apparatus using the single-array detector can be obtained. Here the weighting function applied to the projection data of each row may be the same or different. The correction angle width index can be set with respect to the movement of the imaging region. For example, in the case of imaging a plurality of regions by normal scanning, projection data angle 2Fπ using for back-projection is widened in the region giving greater emphasis on noise amount and narrowed in the region giving greater emphasis on the time resolution. Also since data redundancy is different depending on the position of a pixel as seen in FIG. 9, the correction angle width may differ according to its degree of redundancy in order to use the data effectively. For example, in the high redundancy position the correction angle width is widened, and in the low position it is narrowed.

As for the back projection process (step 105), other than the conventional method, the reconstruction method proposed by the present applicant (JP-A-2004-188163) can also be applied as the 3-dimension back projection process. This method is to simplify the conventional arcsin calculation by calculating the approximated line of the curve indicating the radiation source position to the channel direction position of the parallel beam projection data, and by using this method the time required for the reconstruction process will be drastically reduced compared to the conventional method.

Also while the projection data using the circular orbit scanning was described in the above-mentioned embodiment, it also applicable to helical orbit scanning. However in the case of helical orbit scanning, in the same manner as when an object moves, streaks of artifacts are generated at a corresponding position because of the discontinuity of the data in the scanning data end point when only the filter-correcting 2-dimensional back projection is implemented. So the data interpolation is carried out on the data obtained by the helical orbit to correct it to the circular orbit data as shown in FIG. 2(*b*), and then the filtering correction process is implemented. Such data interpolation is carried out prior to the rearrangement to the parallel beam projection data (step 102) in the reconstruction procedure indicated in FIG. 4. That is, data such as a circular orbit is created first by implementing the interpolation of the data with regard to the feeding direction of the table corresponding to the projection data obtained by the helical orbit scanning. Then the CT image, in the same manner as the circular orbit data, can be obtained by implementing the above-mentioned rearrangement process (step 102), the correction process using the weighting function (step 103), the reconstruction filtering process (step 104) and the back projection process (step 105) to the interpolated projection data.

Also the degree of the artifact generated in the imaging end by the helical orbit scanning is determined by the degree of the discontinuity in an orbit of the X-ray source. This means that the degree of artifact varies according to the moving speed of the object (table feeding speed). Therefore in order to determine correction angle width index $\epsilon$ and index F of projection data angle using for back-projection, it is necessary to consider the feeding speed of the table in addition to the factors to consider in the case of the normal scanning such as the exposure amount of the X-ray, time resolution or noise. For example, when the movement velocity is fast, F should be smaller. By making F smaller the settable maximum value of $\epsilon$ also becomes smaller, but $\epsilon$ should be set as large as possible in order to obtain the corrective effect.

While above-mentioned is the description on an embodiment of the reconstruction method of the present invention using the weighting function to the parallel beam projection data, the present invention is also applicable to the reconstruction method from the fan beam projection data. Hereinafter, the reconstruction method from the fan beam projection data will be described as the second embodiment of the present invention. An example of the procedure of the reconstruction method is indicated in FIG. 4 (*b*).

In this embodiment, the bio-movement correction of the projection data and the correction for eliminating the image distortion due to redundancy are carried out without the rearrangement of the obtained fan beam projection data (step 112). The data correction process is for obtaining weighting function $w(\theta, \gamma)$ to apply to the fan beam based on correction angle width index $\epsilon$ and index F of projection data angle using for back-projection inputted from the input unit, as in the first embodiment. In concrete terms, it is calculated using N which satisfies $2^{(N-1)} \leq F - \epsilon/2 < 2^N$ by the formulas below:

$w(\theta)=0$ if $[\theta < P_0 \pi]$ $w(\theta)=(P_7\pi+\theta)W1/(\epsilon\pi)$ if $[P_0\pi \leq \theta < P_1\pi, \epsilon > 0]$ $w(\theta)=0$ if $[P_0\pi \leq \theta < P_1\pi, \epsilon = 0]$ $w(\theta)=W1*V2*2/\epsilon$ if $[P_1\pi \leq \theta < P_2\pi, \epsilon > 0, V1=0]$ $w(\theta)=((\theta-P_1\pi)*(W1*4/\epsilon)/2\pi)+W1*V2*2/\epsilon$ if $[P_1\pi \leq \theta < P_2\pi, \epsilon > 0, V1 \neq 0]$ $w(\theta)=W1$ if $[P_1\pi \leq \theta < P_2\pi, \epsilon = 0]$ $w(\theta)=W1$ if $[P_1\pi \leq \theta < P_2\pi, \epsilon = 0]$ $w(\theta)=((\theta-P_3\pi)*W1/(\epsilon\pi))+W2$ if $[P_2\pi \leq \theta < P_3\pi, \epsilon > 0]$ $w(\theta)=W2$ if $[P_3\pi \leq \theta < P_4\pi]$ $w(\theta)=((P_4\pi-\theta)*W1/(\epsilon\pi))+W2$ if $[P_4\pi \leq \theta < P_5\pi, \epsilon > 0]$ $w(\theta)=W1*V2*2/\epsilon$ if $[P_5\pi \leq \theta < P_6\pi, \epsilon > 0, V1=0]$ $w(\theta)=((P6\pi-\theta)*(W1*4/\epsilon)/2\pi)+W1*V2*2/\epsilon$ if $[P_5\pi \leq \theta < P_6\pi, \epsilon > 0, V1 \neq 0]$ $w(\theta)=W1$ if $[P_5\pi \leq \theta < P_6\pi, \epsilon = 0]$ $w(\theta)=(P_7\pi-\theta)W1/(\epsilon\pi)$ if $[P_6\pi \leq \theta < P_7\pi, \epsilon > 0]$ $w(\theta)=0$ if $[P_6\pi \leq \theta < P_7\pi, \epsilon = 0]$ $w(\theta)=0$ [Formula 11A]

if $[P_7\pi \leq \theta]$.

Here, the respective parameters in the above formulas are determined by the following respective formulas:

$V1=\epsilon-F+2^{(N-1)}$ if $[\epsilon-F+2^{(N-1)}>0]$ $V2=\epsilon/2-V1$ $M=2^N$ $W1=1/2^N$ $W2=1/2^{(N-1)}$ if $[\epsilon \leq 0]$ $W2=2*W1$ if $[\epsilon>0, F<M]$ $W2=(2*(M-F)+\epsilon)*W1/\epsilon+W1$ if $[\epsilon>0, M \leq F]$ $AA = -F$ $BB = -F + \epsilon$ $CC = M - F$ $DD = M - F + \epsilon$ $EE = F - M - \epsilon$ $FF = F - M$ $GG = F - \epsilon$ $HH = F$ $P_0 = AA$ $P_1 = BB$ if $[F < M/2 + \epsilon/2]$ $P_1 = EE$ if $[M/2 + \epsilon/2 \leq F < M/2 + \epsilon]$ $P_1 = BB$ if $[M/2 + \epsilon \leq F]$ $P_2 = BB$ if $[M/2 + \epsilon/2 \leq F < M/2 + \epsilon]$ $P_2 = EE$ if $[M/2 + \epsilon \leq F < M + \epsilon/2]$ $P_2 = CC$ if $[M + \epsilon/2 \leq F]$ $P_3 = FF$ if $[M/2 + \epsilon/2 \leq F < M]$ $P_3 = CC$ if $[M \leq F < M + \epsilon/2]$ $P_3 = EE$ if $[M + \epsilon/2 \leq F]$ $P_4 = CC$ if $[M/2 + \epsilon/2 \leq F < M]$ $P_4 = FF$ if $[M \leq F < M + \epsilon/2]$ $P_4 = DD$ if $[M + \epsilon/2 \leq F]$ $P_5 = GG$ if $[M/2 + \epsilon/2 \leq F < M/2 + \epsilon]$ $P_5 = DD$ if $[M/2 + \epsilon \leq F < M + \epsilon/2]$ $P_5 = FF$ if $[M + \epsilon/2 \leq F]$ $P_6 = GG$ if $[F < M/2 + \epsilon/2]$ $P_6 = DD$ if $[M/2 + \epsilon/2 \leq F < M/2 + \epsilon]$ $P_6 = GG$ if $[M/2 + \epsilon \leq F]$ $P_7 = HH.$  [Formula 11B]

Alternatively, weighting function Wf(θ, γ) can be expressed with the formula (10) by using the same mode of expression as weighting function Wp(θ) with regard to the above-mentioned parallel beam, and also with the formula (10') using the non-linear sub weight.

[Formulas 12]

$$Wf(\theta, \gamma) = G \cdot \left\{ Ws\left(\frac{\theta - \gamma}{2\pi} - \theta_{c1}, \eta, \varepsilon\right) + Ws\left(\frac{\theta - \gamma}{2\pi} - \theta_{c2}, \eta, \varepsilon\right) \right\} \quad (10)$$

$$Wf(\theta, \gamma) = \quad (10')$$
$$G \cdot \left\{ NL\left(Ws\left(\frac{\theta - \gamma}{2\pi} - \theta_{c1}, \eta, \varepsilon\right)\right) + NL\left(Ws\left(\frac{\theta - \gamma}{2\pi} - \theta_{c2}, \eta, \varepsilon\right)\right) \right\}$$

An example of the weighting function for the fan beam back projection by the present embodiment will be illustrated in FIG. 10. While the diagram is shown by a sinogram, by replacing this weighting function with the parallel beam and looking at it from the perspective that γ=0, the weighting function shape can be changed according to the value of F and ε as shown in FIG. 7 (a)~(c) and FIG. 8 (a)~(c). Here, when γ=0, in the case that F=M/2+ε/2 or F=M/2+ε the weighting function shape would be as shown in FIG. 7 (c), and in the case that M/2+ε<F<M+ε/2 it would be shown as FIG. 7 (a). Also when M/2+ε<F=M, it would be as shown in FIG. 7 (b). Here, M is M=$2^N$ and N is $2^{(N-1)} \leq F - \epsilon/2 < 2^N$. In this way, the weighting function can change its weighting function shape according to the value of F and ε, an influence caused by the movement can be corrected further as the value of F and ε gets bigger and the noise can be reduced further as the value of ε gets smaller. More satisfactory resulting images can be obtained by changing the value of ε depending on the region.

In the next steps, the reconstruction filtering process is executed by superimposing the reconstruction filtering function in a channel direction with regard to the fan beam projection data being applied to the weighting function obtained as above (step 113), then CT images are obtained by implementing the back projection process accompanying the calculation of the inverse trigonometric function and the distance calculation between the X-ray source and the reconstruction pixels (step 114). As for the reconstruction filtering and the back projection process, heretofore known methods can be adopted.

In this embodiment also, the discontinuity in the end portion of the data can be corrected with a definite corrective effect with any value that the projection data angle using for back-projection have.

This embodiment may be applied either to the reconstruction method for performing the calculation of the inverse trigonometric function and the distance calculation between the X-ray source and the reconstruction pixels without executing the rearrangement process from the fan beam to the parallel beam as shown in FIG. 4 (b), or to the reconstruction method for implementing the rearrangement process to the parallel beam, reconstruction filtering process and back projection process after correcting the fan beam projection data using the weighting function. Also the weighting process of the fan beam projection data can be used as a cutting-out window for the projection data in the continuous scanning or helical scanning. In concrete terms, it can be applied to the interventional radiography for performing surgery or hyperthermia treatment enabling the use of the contrast radiography or CT apparatus as a monitor.

As for the correction angle width and the projection data angle using for back-projection in the process using the above-described weighting function, the value set in advance as a default may be used, or at least one of them may be set arbitrary by the user. Also it is possible to obtain the weighting function to apply in an ex-post manner relating to the acquired projection data, not to obtain the weighting function prior to the imaging based on the correction angle width and/or the projection data angle using for back-projection either being set by the user or as a default. In the ex-post case, the correction angle width and the projection data angle using for back-projection are changed and applied.

It is apparent that the objective of the present invention is achieved from the various embodiments described above. However, these are intended merely for explanation and exemplification, to which the present invention is not limited.

While the tomograph using the X-ray is described in the present embodiment, without being limited to this, the present invention is applicable to tomograph using neutron radiation, positive electron, gamma ray or light. The scanning method is not limited to any of the "first", "second", "third" or "fourth generation" systems, and it may also be applied to multi-tube type CT equipped with a plurality of X-ray sources, cathode scanning CT, electronic beam CT or C-arm type CT. Also, the form of the detector can be applied to any detectors such as a detector being disposed on the cylinder surface with an X-ray source in the center, planar detector, detector disposed on the spherical surface with an X-ray source in the center, or detector disposed on the cylinder surface with the revolving axis in the center.

EMBODIMENTS

In order to compare the conventional reconstruction methods using a weighting function and the reconstruction method of the present invention, motion artifacts and the image SD value were obtained and evaluated. As for the geometry, the one of the cone beam was adopted.

[Simulation 1]

The image was reconstructed using the weight being created by fixing the index of projection data angle using for back-projection as F=1.1 and varying correction angle width index $\epsilon$ as 0.0, 0.2, 0.4, 0.6, and the generation of motion artifacts was verified. The weighting function shape and the reconstructed images are shown in FIG. 12. In the case of correction angle width $\epsilon$=0 as shown in FIG. 12 (a), an intensive motion artifact appears since the slope of the weight is not maintained. In the case of $\epsilon$=0.2 shown in (b) which is comparable to the conventional weight, some improvement can be recognized, yet it is still insufficient. On the other hand, a considerable improvement of motion artifacts was recognized in the reconstruction method (c) and (d) of the present invention.

[Simulation 2]

The generation of motion artifacts was verified by fixing correction angle width index $\epsilon$ as 0.4 and varying index F of projection data angle using for back-projection to 0.8, 0.9, 1.0, 1.1. The generation of motion artifacts was verified also in the conventional reconstruction method by using the weighting function by which the index of projection data angle using for back-projection was varied in the same manner. In the conventional weighting function, when the index of projection data angle using for back-projection is determined, the slope of weight also is automatically determined.

As a result, as shown in FIG. 13, intensive artifacts were generated where the projection data angle using for back-projection was in the vicinity of $2\pi$ in the conventional reconstruction method (b), but in the reconstruction method (a) of the present invention the motion artifacts were stably reduced regardless of the projection data angle using for back-projection.

[Simulation 3]

With regard to the reconstructed image obtained in simulation 2, the image SD value was measured as a noise evaluation. As seen in the result shown in Chart 1, in the reconstruction method of the present invention, the noise amount is somewhat increased compared to the conventional reconstruction method in the case of the index of projection data angle using for back-projection being 1.0, 1.1. However, since the image SD and motion artifacts are in a trade-off relationship, as opposed to the conventional reconstruction method incapable of restraining motion artifacts due to emphasizing the image SD, it is possible to reduce motion artifact considerably in the reconstruction method of the present invention without a significant increase of noise.

CHART 1

| | Projection Data Angle "F" Using for Back-Projection | 0.8 | 0.9 | 1.0 | 1.1 |
|---|---|---|---|---|---|
| Image SD Value | Present Invention | 14.3 | 13.8 | 12.8 | 11.8 |
| | Conventional Method | 14.3 | 13.8 | 11.3 | 11.1 |

Figure 1:
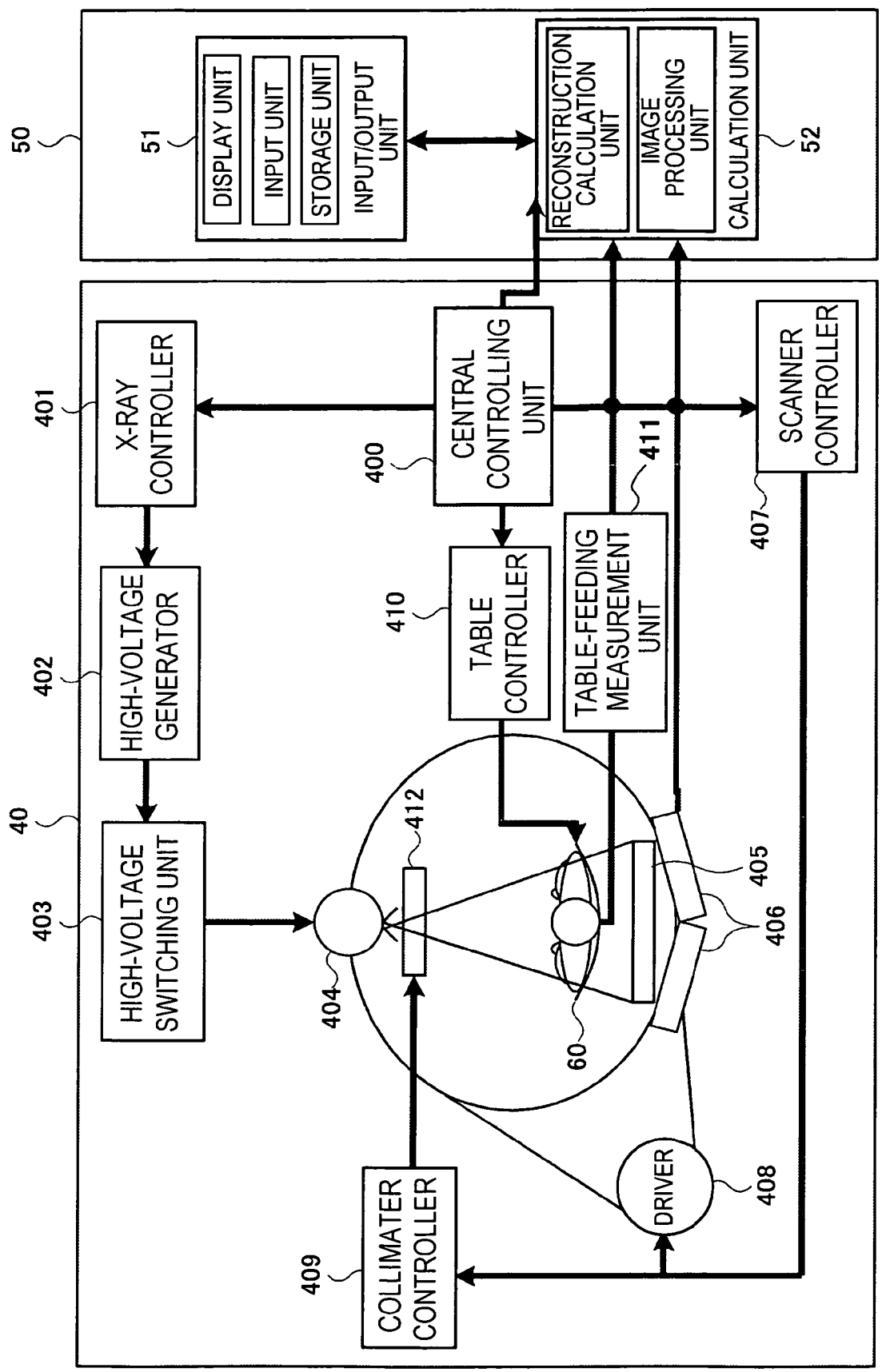
FIG. 1 is a diagram showing the general configuration of the X-ray CT apparatus to which the present invention is applied.
Figure 2:
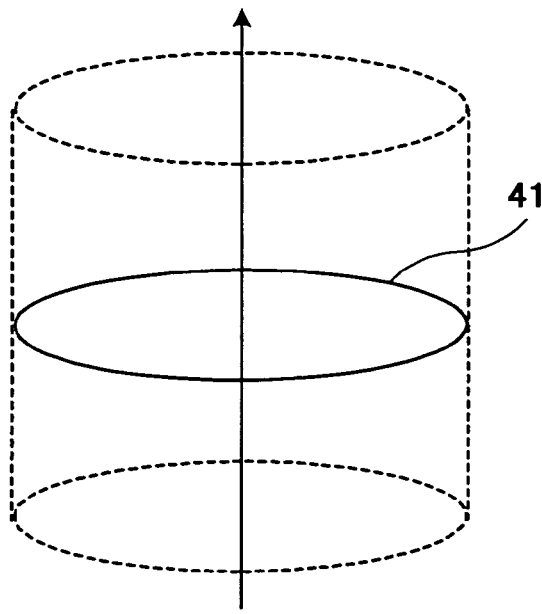
FIGS. 2 (a) and (b) are diagrams explaining the imaging method by which the X-ray CT apparatus of the present invention is adopted.
Figure 2:
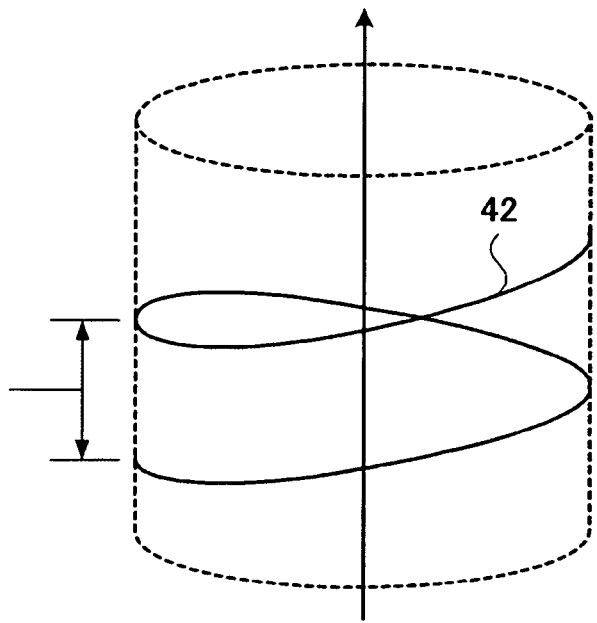
Figure 3:
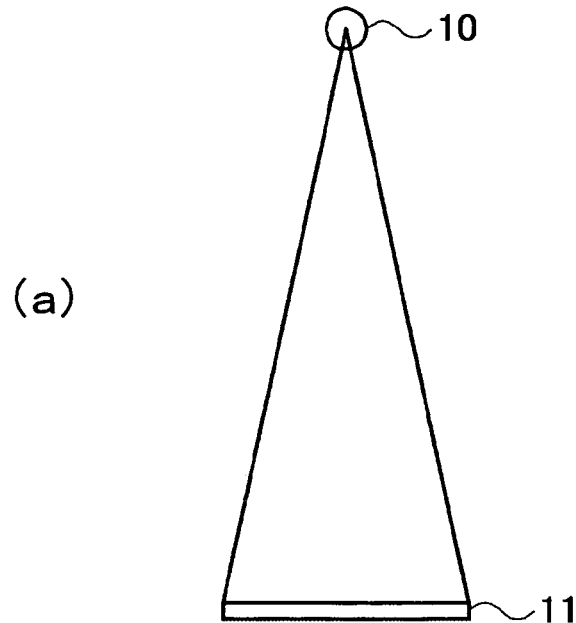
FIGS. 3 (a) and (b) are diagrams showing the detector of the X-ray CT apparatus in the present invention, wherein (a) indicates a single-array detector and (b) a multi-array detector.
Figure 3:
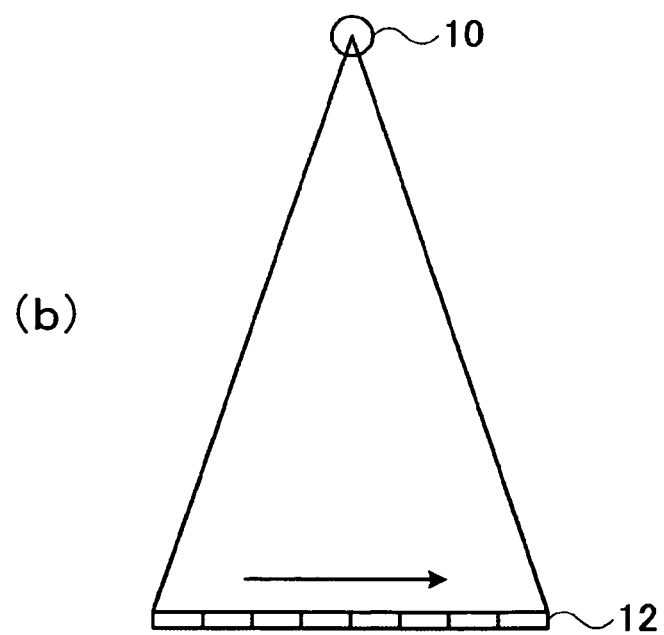
Figure 4:
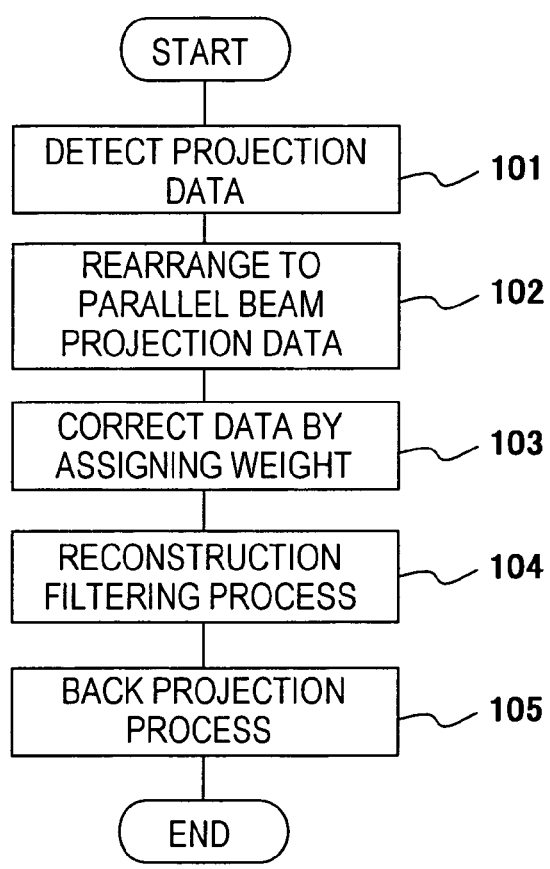
FIGS. 4 (a) and (b) are diagrams showing a procedure of the image reconstruction in the present invention, wherein (a) indicates the first embodiment and (b) the second embodiment.
Figure 4:
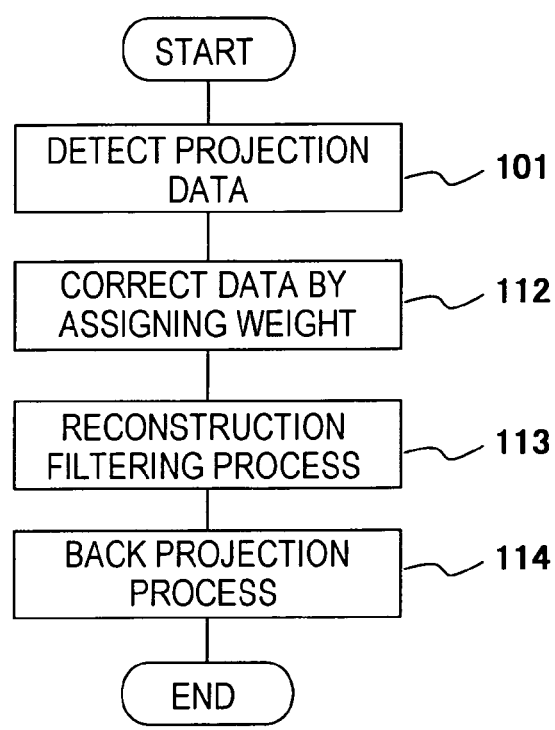
Figure 5:
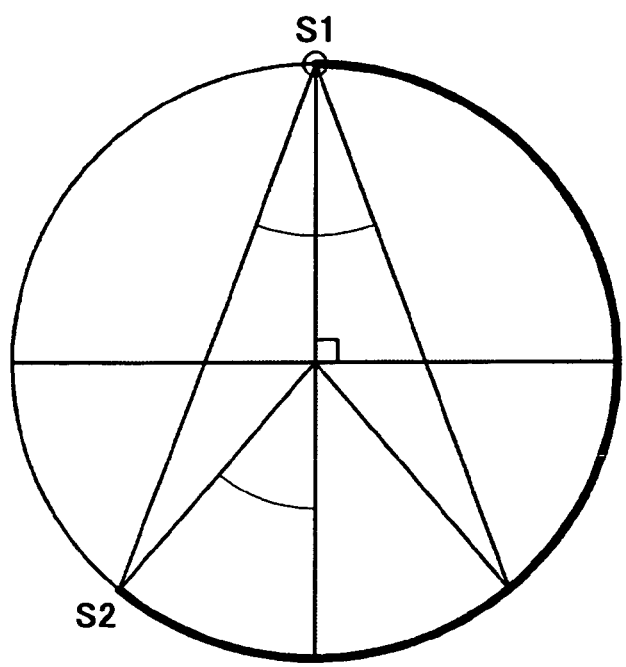
FIGS. 5 (a) and (b) are diagrams illustrating the rearrangement from the fan beam projection data to the parallel beam projection data.
Figure 5:
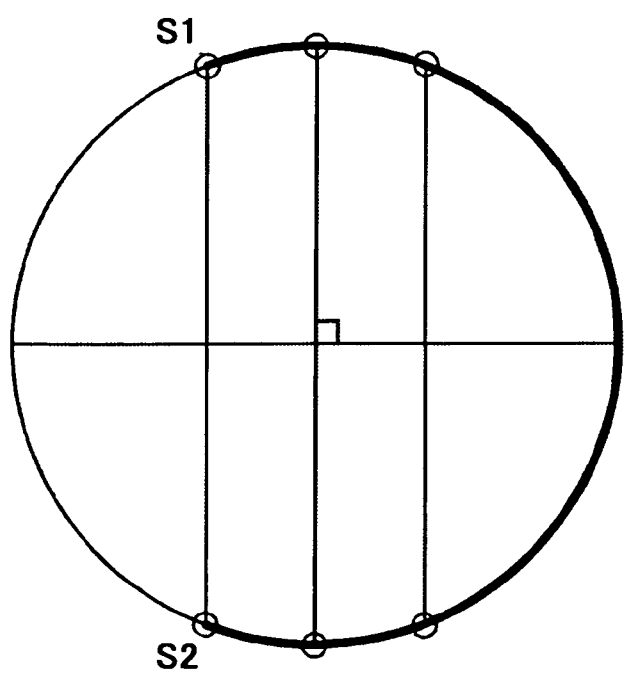
Figure 6:
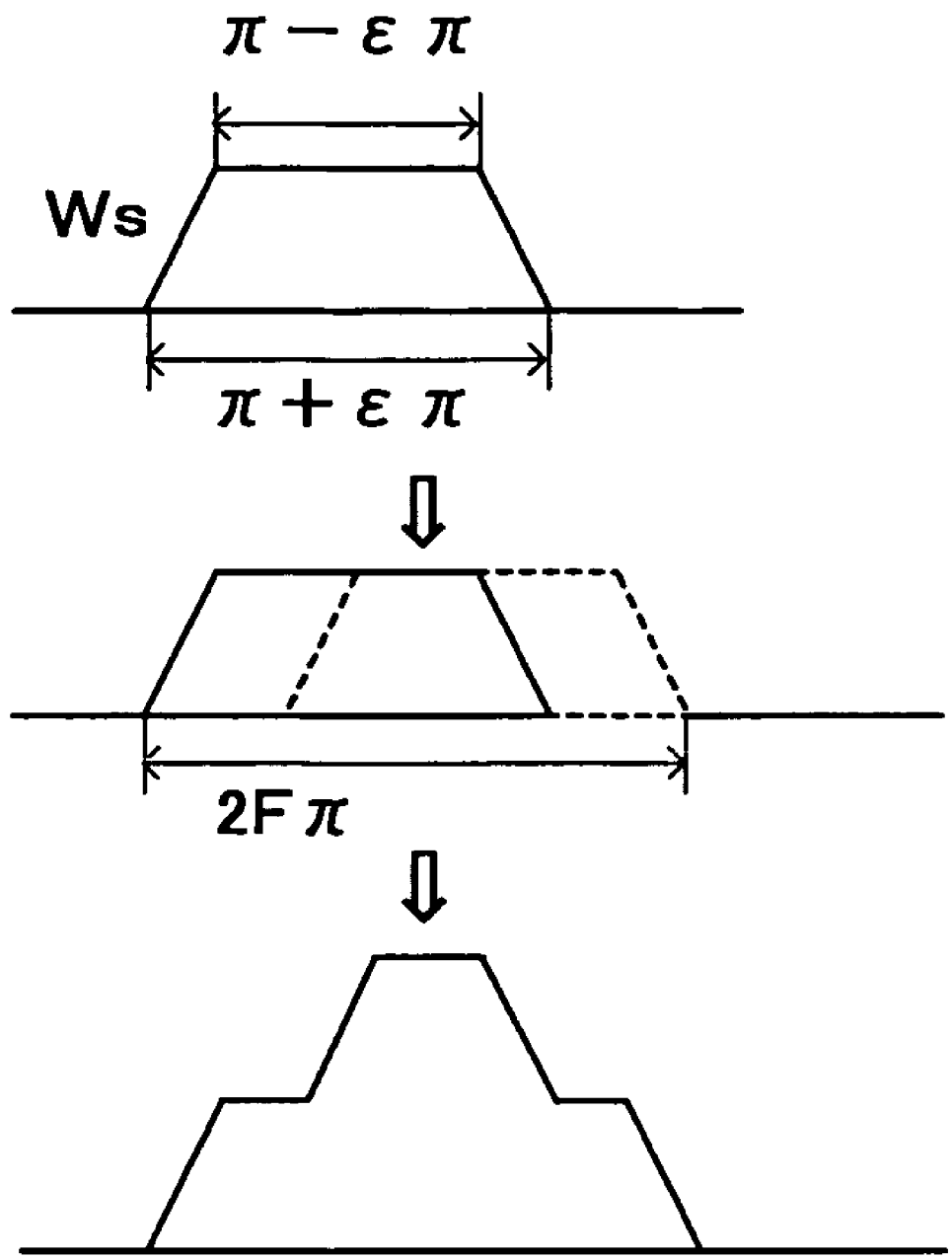
FIG. 6 is a diagram illustrating the concept of the weighting function being adopted by the tomogram reconstruction method of the present invention.
Figure 7:
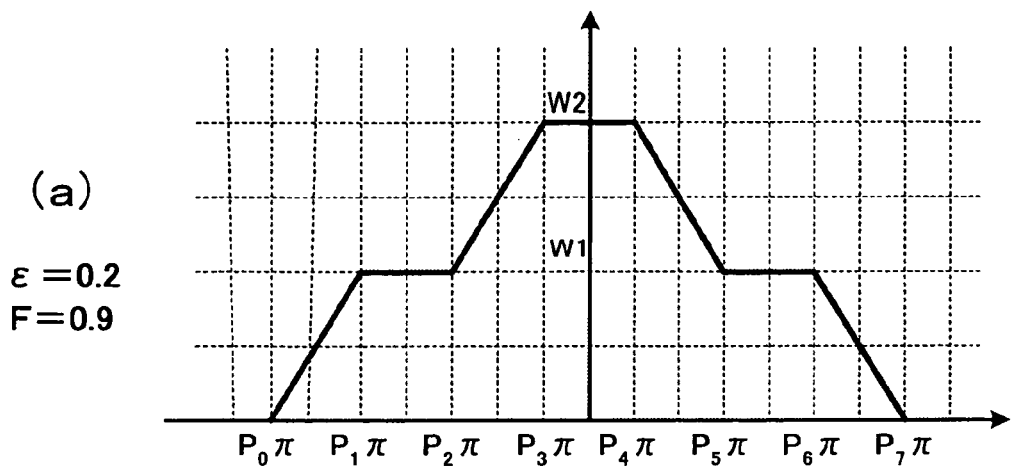
FIG. 7 (a)~(c) are diagrams showing an example of the weighting function for the parallel beam back projection adopted by the tomogram reconstruction method of the present invention.
Figure 7:
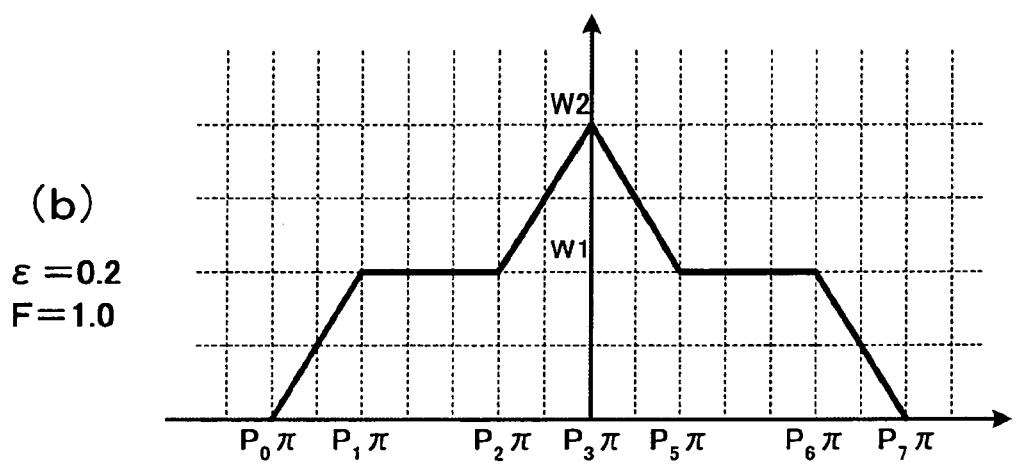
Figure 7:
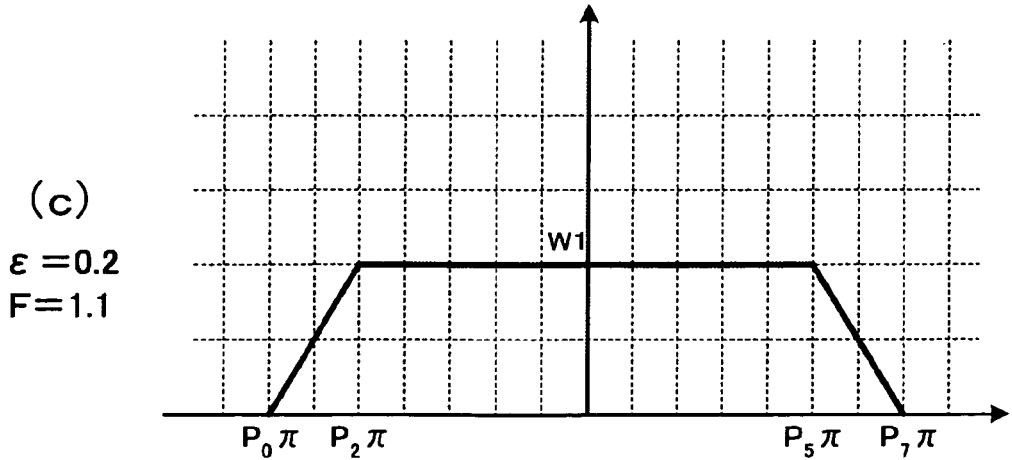
Figure 8:
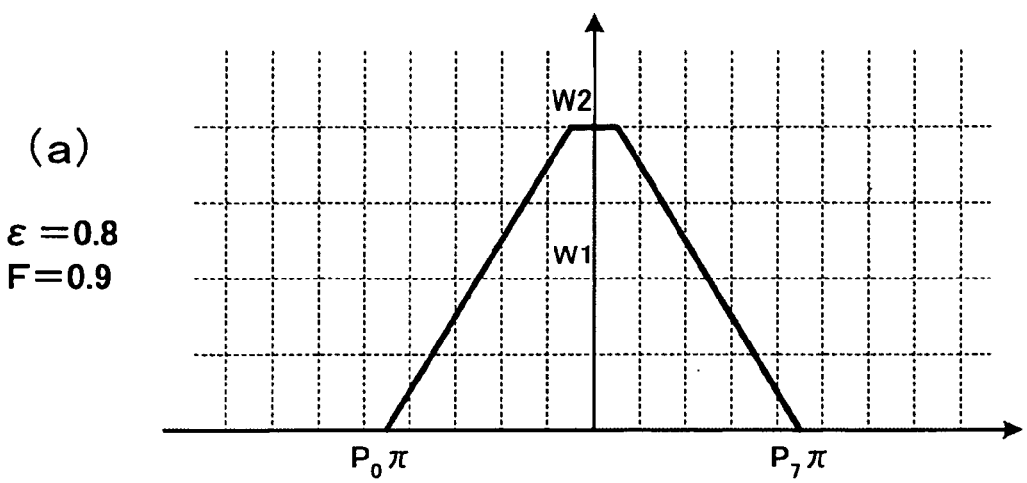
FIGS. 8 (a)~(c) are diagrams showing an example of the weighting function for the parallel beam back projection adopted by the tomogram reconstruction method of the present invention.
Figure 8:
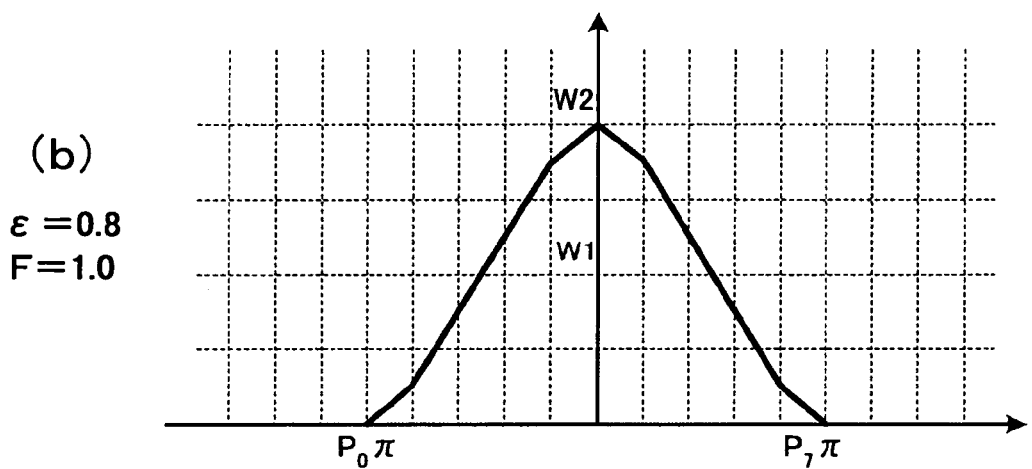
Figure 8:
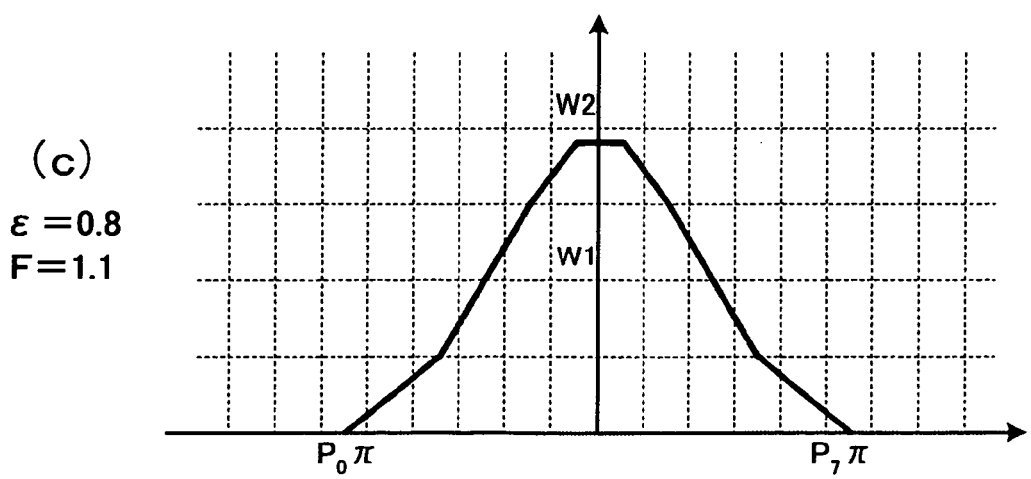
Figure 9:
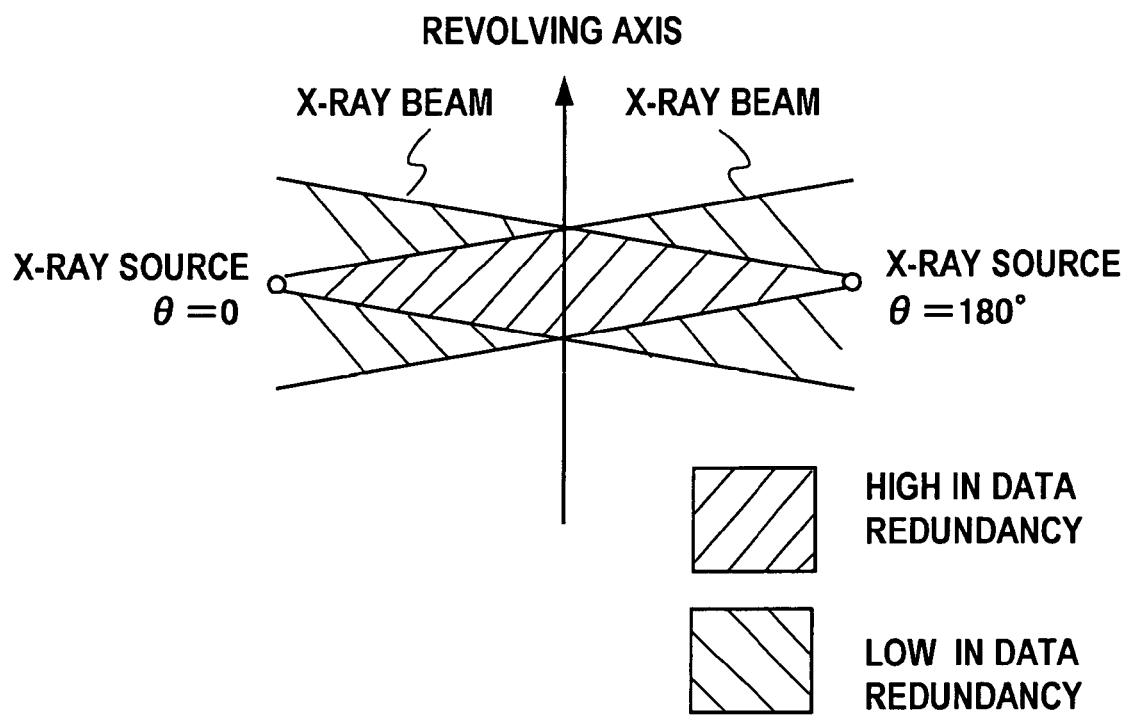
FIG. 9 is a diagram illustrating the case of applying the weighting functions that are different in every row in a CT apparatus using a multi-array detector.
Figure 10:
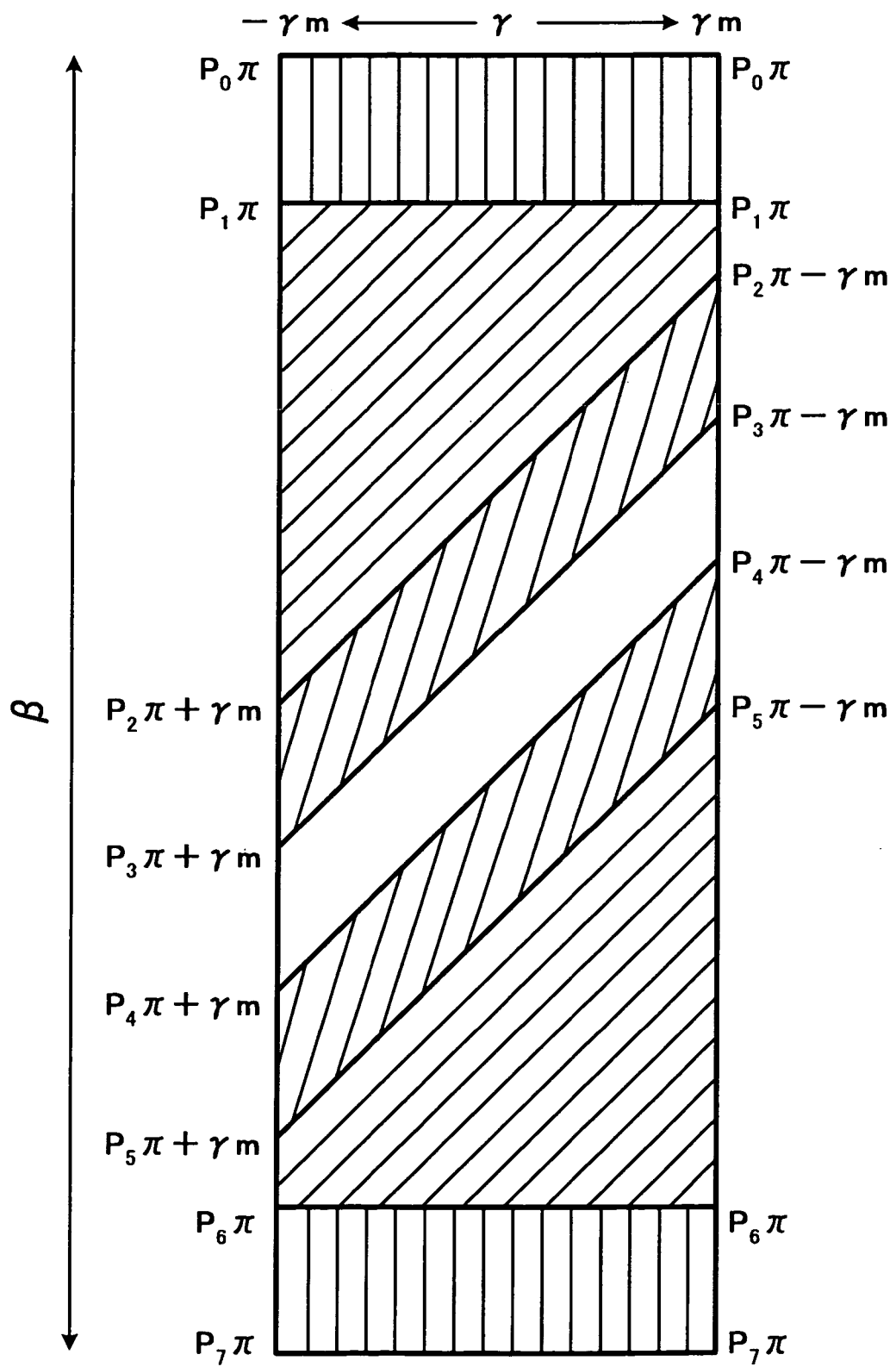
FIG. 10 is a diagram showing an example of the weighting function for the fan beam back projection adopted in the tomogram reconstruction method of the present invention.
Figure 11:
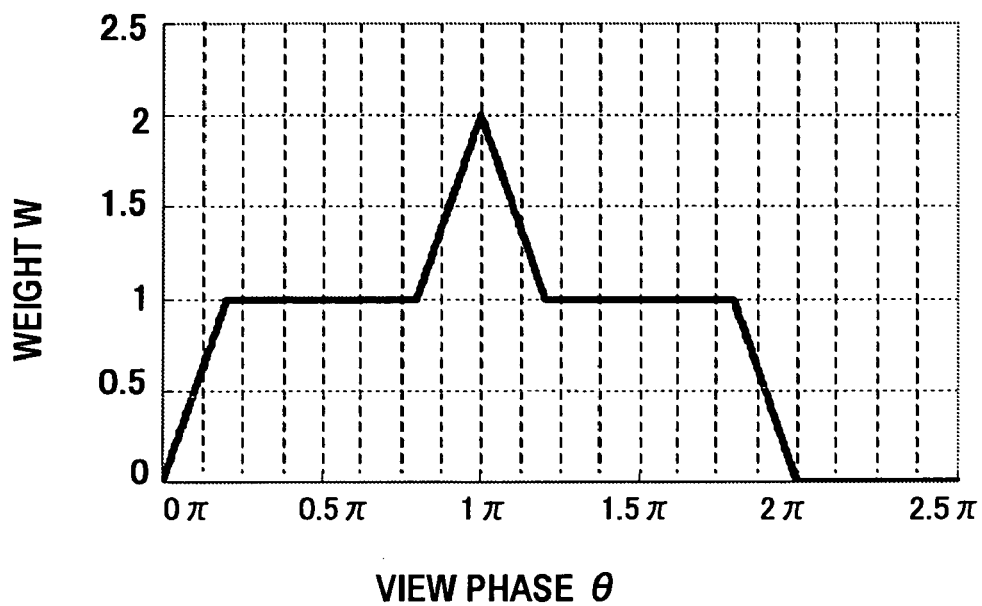
FIGS. 11 (a) and (b) are diagrams illustrating the configuration of the weighting function being adopted by the present invention.
Figure 11:
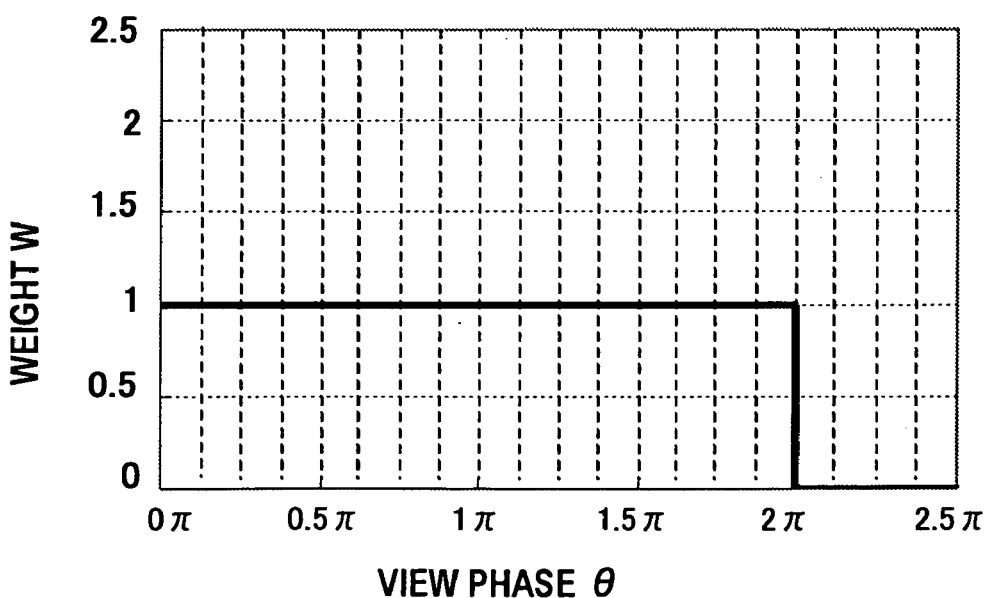
Figure 12:
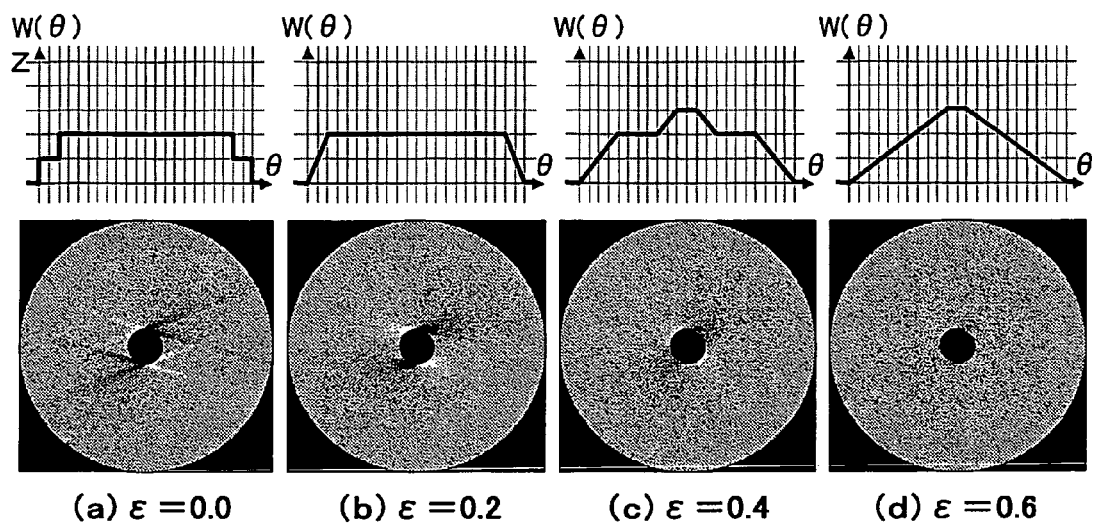
FIG. 12 is a diagram showing the relationship between the weighting function shape and the motion artifact in the reconstructed image.
Figure 13:
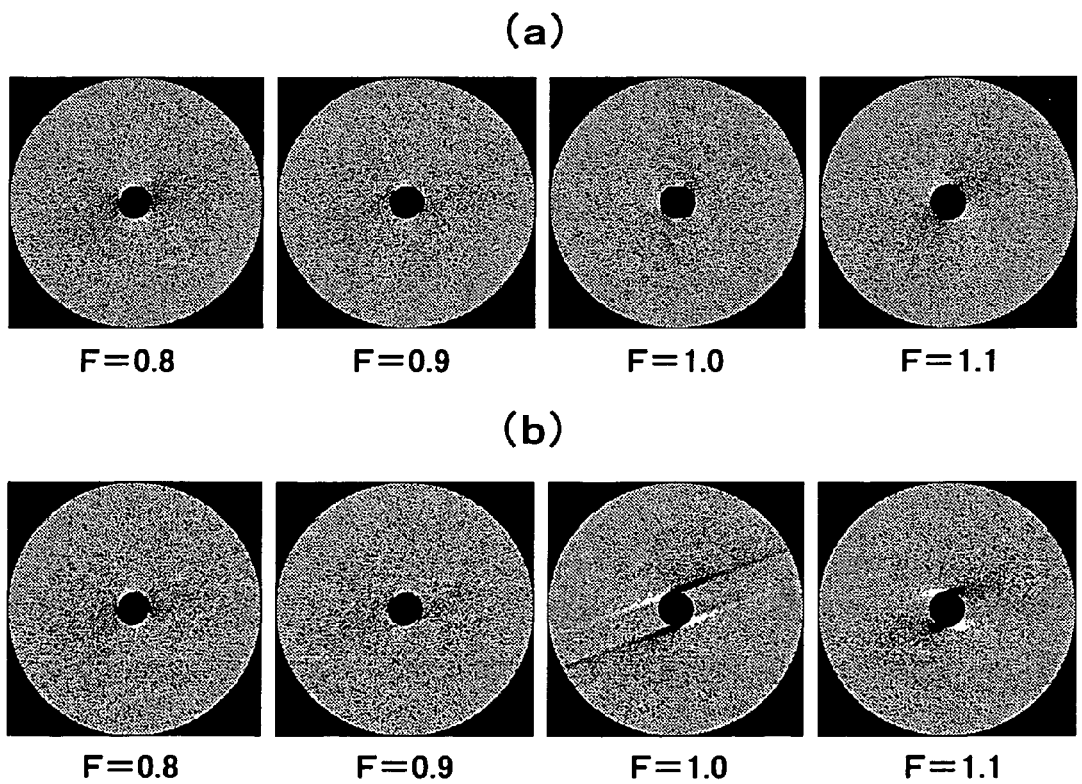
FIGS. 13 (a) and (b) are diagrams showing the comparison of the reconstructed image by the conventional reconstruction method and the one by the reconstruction method of the present invention.
Figure 14:
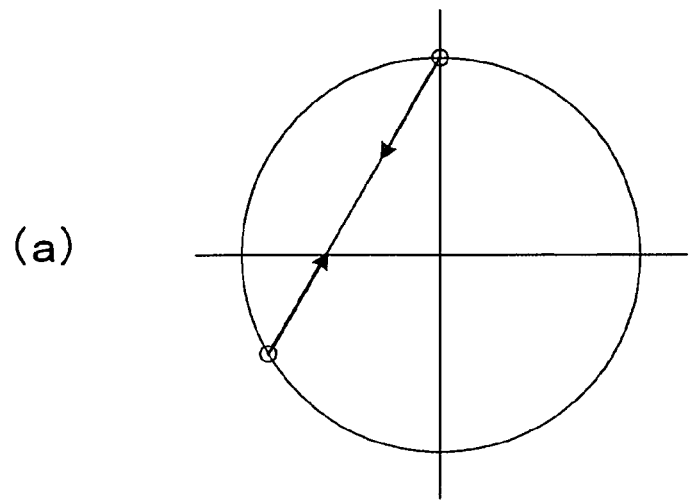
FIGS. 14 (a)~(c) are diagrams for explaining the redundancy in the X-ray CT.
Figure 14:
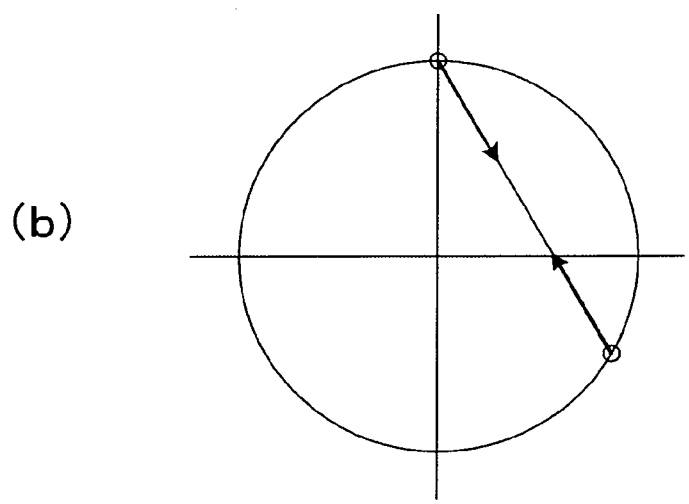
Figure 14:
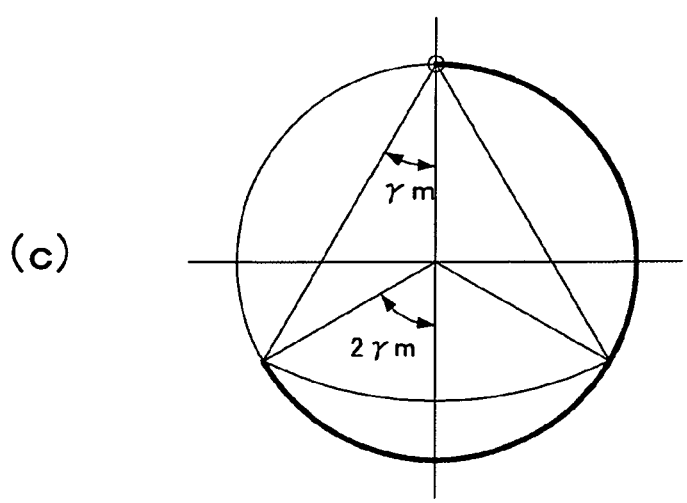
Figure 15:
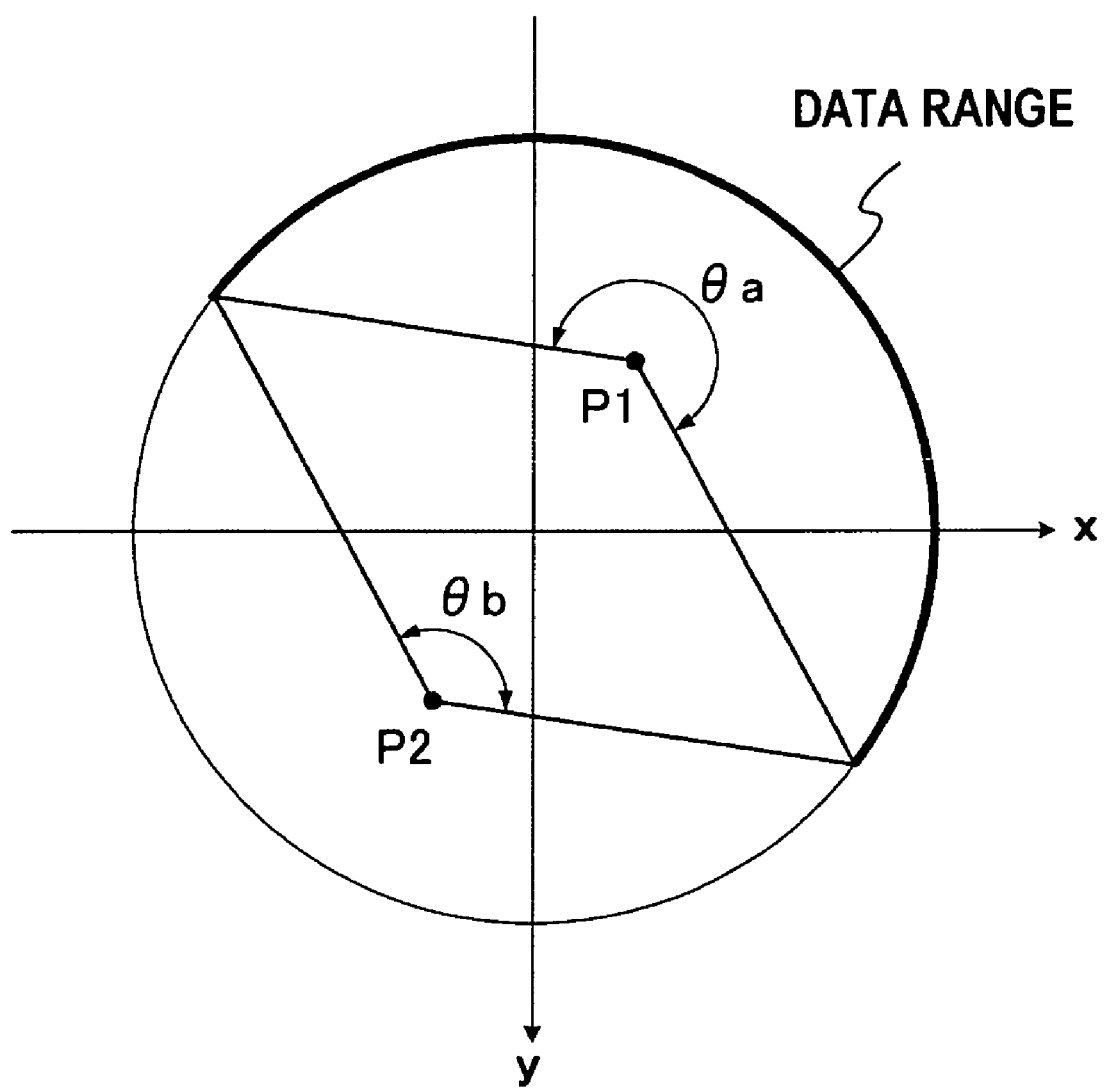
FIG. 15 is a diagram for illustrating the difference of the redundancy by the pixels in the case of implementing the back projection from the data of the minimum projection data angle using for back-projection being $\pi+2\gamma m$.
Figure 16:
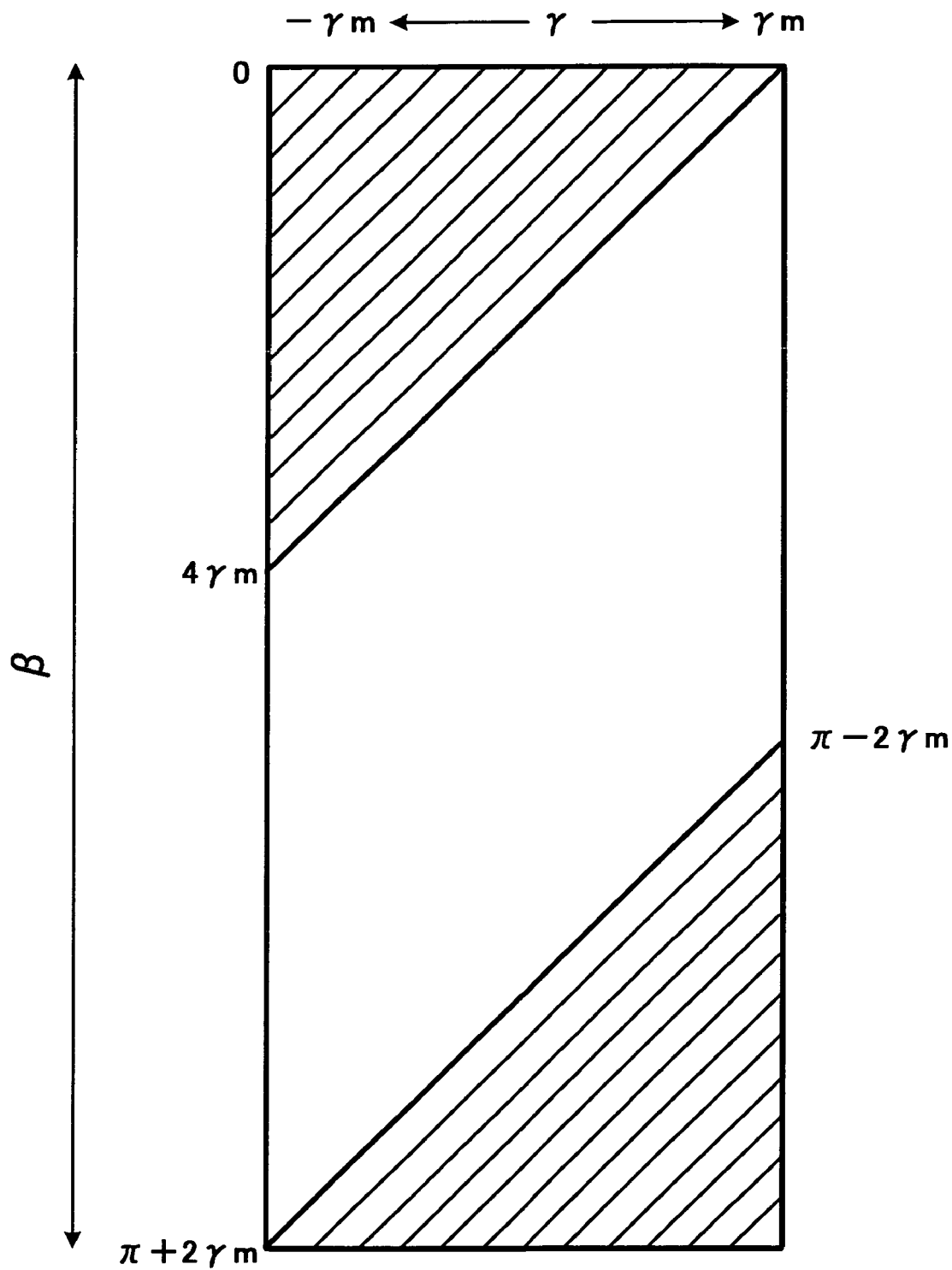
FIG. 16 is a diagram showing an example of a sinogram indicating the minimum complete data set.
Figure 17:
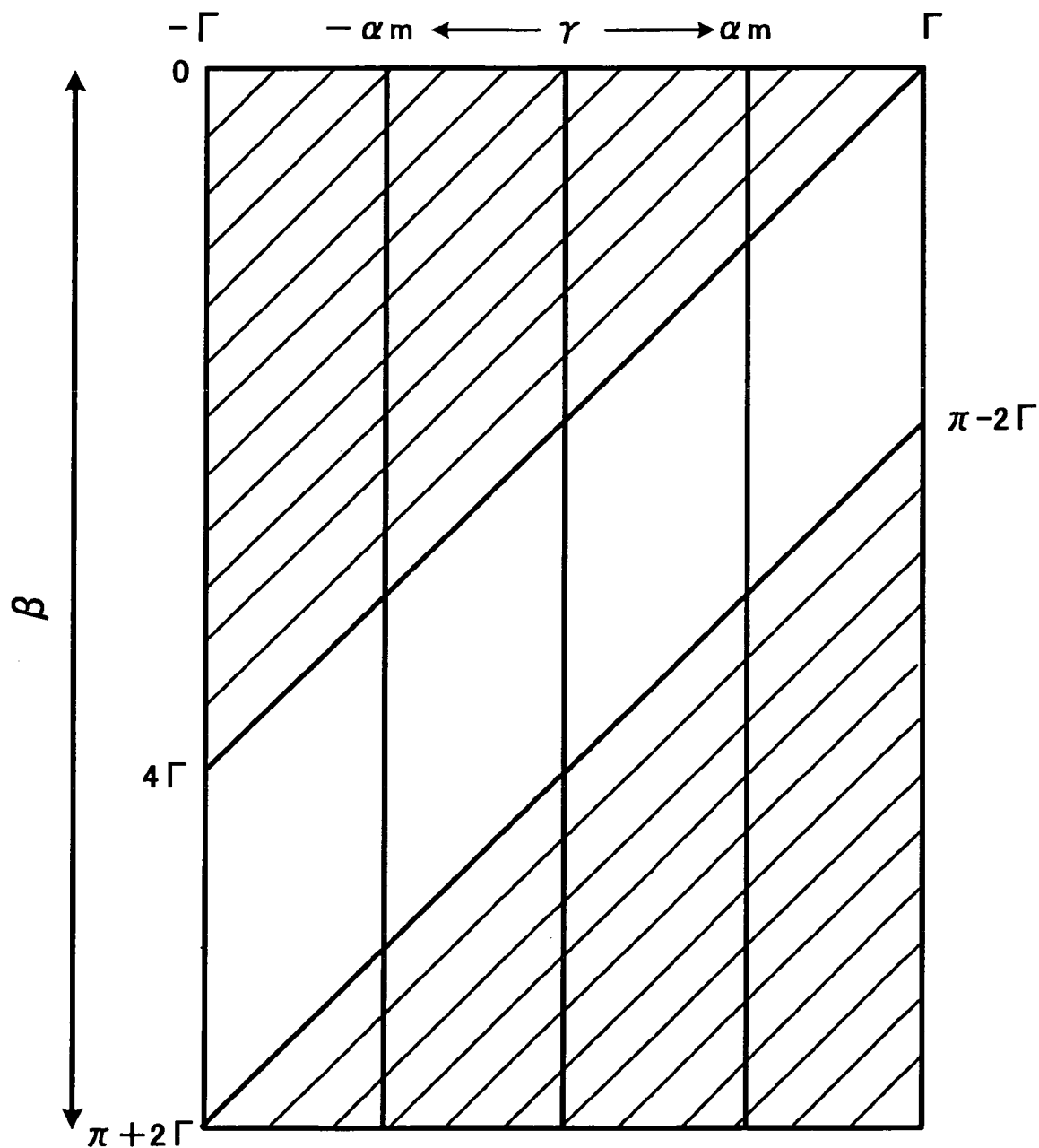
FIG. 17 is a diagram showing the conventional weighting function to which the different weight is given relating to the two triangle regions in the revolving axis direction, while the sinogram is divided into less than three regions including the two triangle regions on a virtual sinogram.
Figure 18:
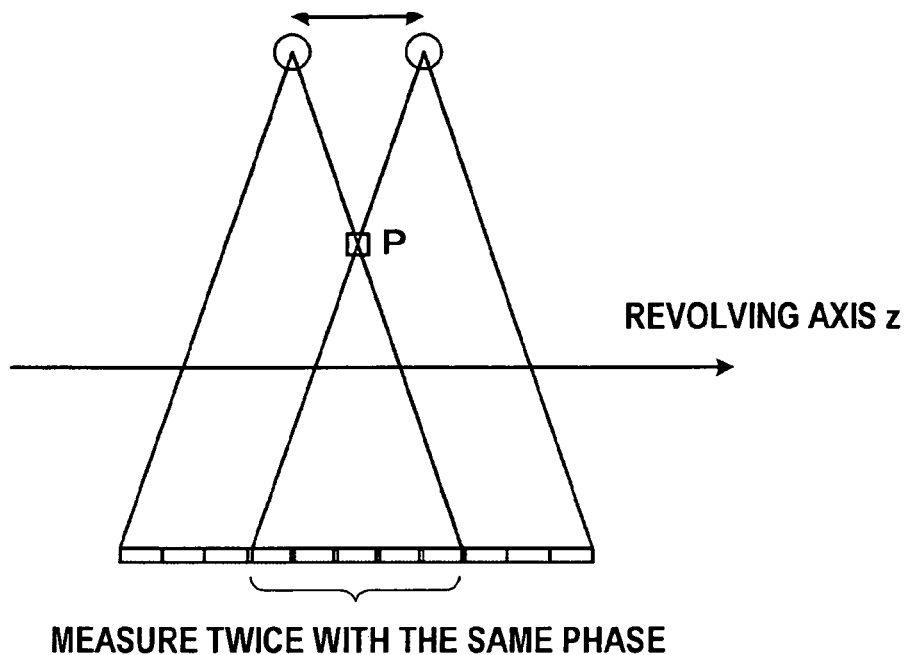
FIG. 18 is a diagram for illustrating the relationship between the image noise and the imaging time.
Figure 18:
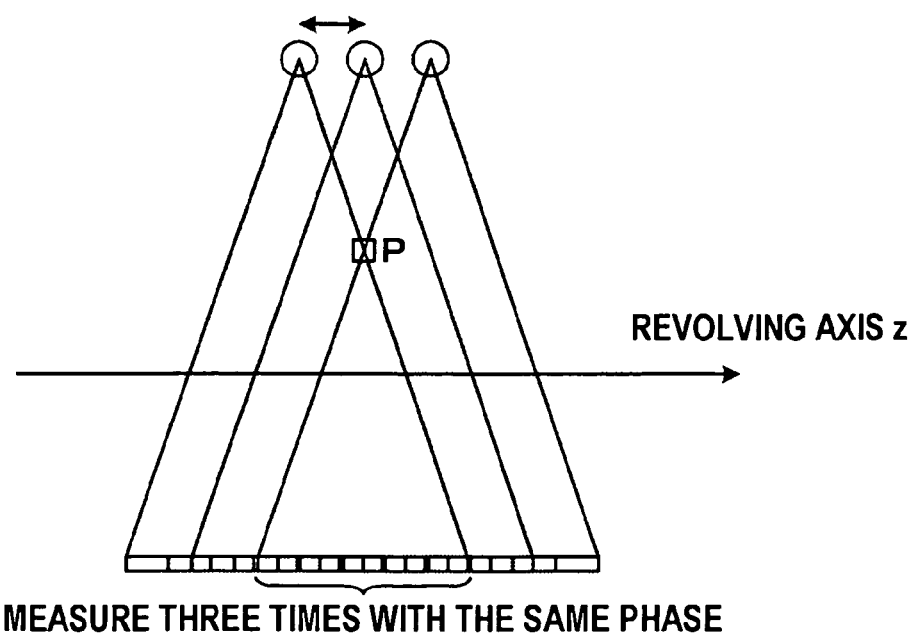
Figure 19:
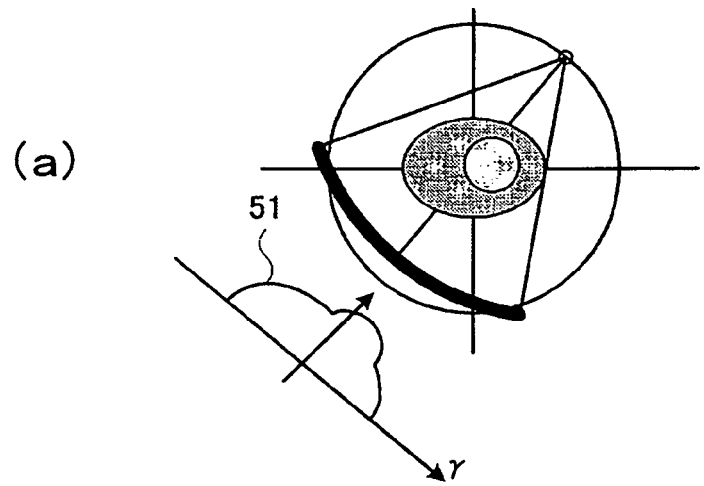
FIG. 19 (a)~(c) are diagrams for illustrating the imaging time and the movement of an object being examined.
Figure 19:
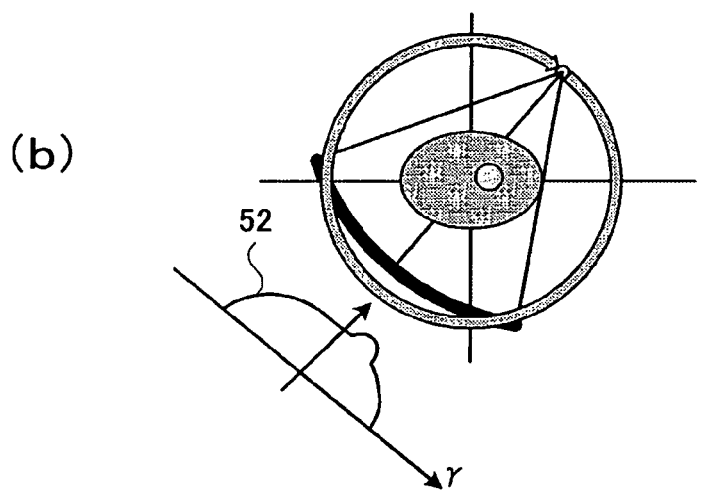
Figure 19:
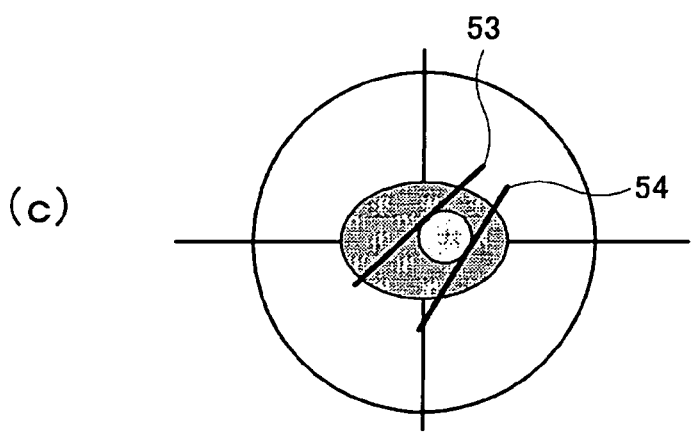

The invention claimed is:

1. A tomogram reconstruction method making a radiation source and a detector disposed to be opposite to each other interposing a scanning object therebetween revolve around a predetermined revolving axis, detecting the penetrated radiation irradiated from the radiation source and transmitted through the object, and creating a tomogram of the region of interest of the object from the detected projection data including:
   a step for obtaining the weighting factor in compliance with a correction angle width and a projection data angle using for back-projection of the projection data;
   a step for obtaining the projection data on which the weighting process based on the weighting factor relating to said projection data is implemented and weighted; and
   a step for reconstructing the tomogram using the weighted projection data.

2. The tomogram reconstruction method according to claim 1, including:
   a step for setting correction angle width and/or the projection data angle for back-projection; and
   a step for setting the value of the other step out of the correction angle width or the projection data angle for back-projection based on the value of the set width in the previous step.

3. The tomogram reconstruction method according to claim 2, wherein the correction angle width and the projection data angle for back-projection are set to be $0 \leq \epsilon \leq \pi \neq (2F-1)$, $\epsilon \neq 2F - 2^{ceil(log2F)}$, when the correction angle width is set as $\epsilon\pi$ and the projection data angle for back-projection as $2F\pi$.

4. The tomogram reconstruction method according to claim 2, wherein the correction angle width is set corresponding to the range of the region for correcting the discontinuity of data in the end portion of the projection data.

5. The tomogram reconstruction method according to claim 2, wherein the correction angle width is changed according to the size of noise quantity in the reconstructed image.

6. The tomogram reconstruction method according to claim 2, wherein the correction angle width is changed according to the size of the motion artifact in the reconstructed image.

7. The tomogram reconstruction method according to claim 2, wherein the correction angle width is increased or decreased by making it directly proportional to the projection data angle for back-projection.

8. The tomogram reconstruction method according to claim 2, wherein the projection data angle for back-projection is set at an arbitrary angle that is more than the data width, equal to $\pi+$ twice the value of the maximum fan angle, of the minimum complete data set.

9. The tomogram reconstruction method according to claim 1, wherein the weighting function is such that the weight in the discontinuity region including the end portion of the data is smaller than the weight in the other region equivalent of the relevant discontinuity region.

10. The tomogram reconstruction method according to claim 9, wherein the weighting function is created by adding and normalizing the first sub weighting function and the second sub weighting function which is created by shifting the first sub weighting function for a predetermined phase.

11. The tomogram reconstruction method according to claim 10, wherein the sub weighting function has the trapezoidal shape of which the upper hem is $[\pi-\epsilon\pi]$ and the bottom is $[\pi+\epsilon\pi]$.

12. The tomogram reconstruction method according to claim 1 further comprises a step for performing a rearrangement process to rearrange the fan beam radiated from the radiation source to the parallel beam, wherein weighting functions $w(\theta)$ for reconstructing with the parallel beam when the revolution phase at the time of detecting the projection data is set as $\theta$ and using N which can be obtained from the correction angle width $\epsilon\pi$[rad] and $2^{(N-1)} \leq F-\epsilon/2 < 2^N$, where N is an integer of more than 0, are determined as follows:

$w(\theta)=0$ if $[\theta<P_0\pi]$ $w(\theta)=(P_7\pi+\theta)W1/(\epsilon\pi)$ if $[P_0\pi \leq \theta<P_1\pi, \epsilon>0]$ $w(\theta)=0$ if $[P_0\pi \leq \theta<P_1\pi, \epsilon=0]$ $w(\theta)=W1*V2*2/\epsilon$ if $[P_1\pi \leq \theta<P_2\pi, \epsilon>0, V1=0]$ $w(\theta)=((\theta-P_1\pi)*(W1*4/\epsilon)/2\pi)+W1*V2*2/\epsilon$ if $[P_1\pi \leq \theta<P_2\pi, \epsilon>0, V1 \neq 0]$ $w(\theta)=W1$ if $[P_1\pi \leq \theta<P_2\pi, \epsilon=0]$ $w(\theta)=W1$ if $[P_1\pi \leq \theta<P_2\pi, \epsilon=0]$ $w(\theta)=((\theta-P_3\pi)*W1/(\epsilon\pi))+W2$ if $[P_2\pi \leq \theta<P_3\pi, \epsilon>0]$ $w(\theta)=W2$ if $[P_3\pi \leq \theta<P_4\pi]$ $w(\theta)=((P_4\pi-\theta)*W1/(\epsilon\pi))+W2$ if $[P_4\pi \leq \theta<P_5\pi, \epsilon>0]$ $w(\theta)=W1*V2*2/\epsilon$ if $[P_5\pi \leq \theta<P_6\pi, \epsilon>0, V1=0]$ $w(\theta)=((P6\pi-\theta)*(W1*4/\epsilon)/2\pi)+W1*V2*2/\epsilon$ if $[P_5\pi \leq \theta<P_6\pi, \epsilon>0, V1 \neq 0]$ $w(\theta)=W1$ if $[P_5\pi \leq \theta<P_6\pi, \epsilon=0]$ $w(\theta)=(P_7\pi-\theta)W1/(\epsilon\pi)$ if $[P_6\pi \leq \theta<P_7\pi, \epsilon>0]$ $w(\theta)=0$ if $[P_6\pi \leq \theta<P_7\pi, \epsilon=0]$ $w(\theta)=0$ if $[P_7\pi \leq \theta]$,    [Formula 1A]

and the respective parameters in the above formulas are determined by the following respective formulas:

$V1=\epsilon-F+2^{(N-1)}$ if $[\epsilon-F+2^{(N-1)}>0]$ $V2=\epsilon/2-V1$ $M=2^N$ $W1=1/2^N$ $W2=1/2^{(N-1)}$ if $[\epsilon \leq 0]$ $W2=2*W1$ if $[\epsilon>0, F<M]$ $W2=(2*(M-F)+\epsilon)*W1/\epsilon+W1$ if $[\epsilon>0, M \leq F]$ $AA=-F$ $BB=-F+\epsilon$ $CC = M-F$ $DD = M-F+\epsilon$ $EE = F-M-\epsilon$ $FF = F-M$ $GG = F-\epsilon$ $HH = F$ $Po = AA$ $P_1 = BB$ if $[F<M/2+\epsilon/2]$ $P_1 = EE$ if $[M/2+\epsilon/2 \leq F<M/2+\epsilon]$ $P_1 = BB$ if $[M/2+\epsilon \leq F]$ $P_2 = BB$ if $[M/2+\epsilon/2 \leq F<M/2+\epsilon]$ $P_2 = EE$ if $[M/2+\epsilon \leq F<M+\epsilon/2]$ $P_2 = CC$ if $[M+\epsilon/2 \leq F]$ $P_3 = FF$ if $[M/2+\epsilon/2 \leq F<M]$ $P_3 = CC$ if $[M \leq F<M+\epsilon/2]$ $P_3 = EE$ if $[M+\epsilon/2 \leq F]$ $P_4 = CC$ if $[M/2+\epsilon/2 \leq F<M]$ $P_4 = FF$ if $[M \leq F<M+\epsilon/2]$ $P_4 = DD$ if $[M+\epsilon/2 \leq F]$ $P_5 = GG$ if $[M/2+\epsilon/2 \leq F<M/2+\epsilon]$ $P_5 = DD$ if $[M/2+\epsilon \leq F<M+\epsilon/2]$ $P_5 = FF$ if $[M+\epsilon/2 \leq F]$ $P_6 = GG$ if $[F<M/2+\epsilon/2]$ $P_6 = DD$ if $[M/2+\epsilon/2 \leq F<M/2+\epsilon]$ $P_6 = GG$ if $[M/2+\epsilon \leq F]$ $P_7 = HH$ [Formula 1B].

13. The tomogram reconstruction method according to claims 1 or 2, wherein weighting functions $w(\theta, \gamma)$ for the fan beam reconstruction in the case that the projection phase of the fan beam is set as $\theta$ and the fan angle is set as $\gamma$, using N which can be obtained from the correction angle width $\epsilon\pi$ [rad] and $2^{(N-1)} \leq F-\epsilon/2 < 2^N$, where N is an integer of more than 0, are determined as follows:

$w(\theta) = 0$ if $[\theta < Po\pi]$ $w(\theta) = (P_7\pi + \theta)W1/(\epsilon\pi)$ if $[Po\pi \leq \theta < P_1\pi, \epsilon > 0]$ $w(\theta) = 0$ if $[Po\pi \leq \theta < P_1\pi, \epsilon = 0]$ $w(\theta) = W1*V2*2/\epsilon$ if $[P_1\pi \leq \theta < P_2\pi, \epsilon > 0, V1=0]$ $w(\theta) = ((\theta-P_1\pi)*(W1*4/\epsilon)/2\pi) + W1*V2*2/\epsilon$ if $[P_1\pi \leq \theta < P_2\pi, \epsilon > 0, V1 \neq 0]$ $w(\theta) = W1$ if $[P_1\pi \leq \theta < P_2\pi, \epsilon = 0]$ $w(\theta) = W1$ if $[P_1\pi \leq \theta < P_2\pi, \epsilon = 0]$ $w(\theta) = ((\theta-P_3\pi)*W1/(\epsilon\pi)) + W2$ if $[P_2\pi \leq \theta < P_3\pi, \epsilon > 0]$ $w(\theta) = W2$ if $[P_3\pi \leq \theta < P_4\pi]$ $w(\theta) = ((P_4\pi-\theta)*W1/(\epsilon\pi)) + W2$ if $[P_4\pi \leq \theta < P_5\pi, \epsilon > 0]$ $w(\theta) = W1*V2*2/\epsilon$ if $[P_5\pi \leq \theta < P_6\pi, \epsilon > 0, V1=0]$ $w(\theta) = ((P6\pi-\theta)*(W1*4/\epsilon)/2\pi) + W1*V2*2/\epsilon$ if $[P_5\pi \leq \theta < P_6\pi, \epsilon > 0, V1 \neq 0]$ $w(\theta) = W1$ if $[P_5\pi \leq \theta < P_6\pi, \epsilon = 0]$ $w(\theta) = (P_7\pi-\theta)W1/(\epsilon\pi)$ if $[P_6\pi \leq \theta < P_7\pi, \epsilon > 0]$ $w(\theta) = 0$ if $[P_6\pi \leq \theta < P_7\pi, \epsilon = 0]$ $w(\theta) = 0$ if $[P_7\pi \leq \theta]$, [Formula 2A]

and the respective parameters in the above formulas are determined by the following respective formulas:

$V1 = \epsilon - F + 2^{(N-1)}$ if $[\epsilon - F + 2^{(N-1)} > 0]$ $V2 = \epsilon/2 - V1$ $M = 2^N$ $W1 = 1/2^N$ $W2 = 1/2^{(N-1)}$ if $[\epsilon \leq 0]$ $W2 = 2*W1$ if $[\epsilon > 0, F<M]$ $W2 = (2*(M-F)+\epsilon)*W1/\epsilon + W1$ if $[\epsilon > 0, M \leq F]$ $AA = -F$ $BB = -F+\epsilon$ $CC = M-F$ $DD = M-F+\epsilon$ $EE = F-M-\epsilon$ $FF = F-M$ $GG = F-\epsilon$ $HH = F$ $Po = AA$ $P_1 = BB$ if $[F<M/2+\epsilon/2]$ $P_1 = EE$ if $[M/2+\epsilon/2 \leq F<M/2+\epsilon]$ $P_1 = BB$ if $[M/2+\epsilon \leq F]$ $P_2 = BB$ if $[M/2+\epsilon/2 \leq F<M/2+\epsilon]$ $P_2 = EE$ if $[M/2+\epsilon \leq F<M+\epsilon/2]$ $P_2 = CC$ if $[M+\epsilon/2 \leq F]$ $P_3 = FF$ if $[M/2+\epsilon/2 \leq F<M]$ $P_3 = CC$ if $[M \leq F<M+\epsilon/2]$ $P_3 = EE$ if $[M+\epsilon/2 \leq F]$ $P_4 = CC$ if $[M/2+\epsilon/2 \leq F<M]$ $P_4 = FF$ if $[M \leq F<M+\epsilon/2]$ $P_4 = DD$ if $[M+\epsilon/2 \leq F]$ $P_5 = GG$ if $[M/2+\epsilon/2 \leq F < M/2+\epsilon]$ $P_5 = DD$ if $[M/2+\epsilon \leq F < M+\epsilon/2]$ $P_5 = FF$ if $[M+\epsilon/2 \leq F]$ $P_6 = GG$ if $[F < M/2+\epsilon/2]$ $P_6 = DD$ if $[M/2+\epsilon/2 \leq F < M/2+\epsilon]$ $P_6 = GG$ if $[M/2+\epsilon \leq F]$ $P_7 = HH$ [Formula 2B].

14. The tomogram reconstruction method according to claim 1, wherein the projection data is detected as moving an object in the revolving axis direction along with the revolution of the radiation source and the detector, including a step for interpolating said projection data and creating the projection data of the side that is orthogonal to the revolving axis.

15. A tomograph comprising:
a radiation source and a detector disposed to be opposite to each other interposing a scanning object therebetween;
a reconstruction means for creating a tomogram of a region of interest of an object from the projection data being detected by the detector; and
an imaging control means for controlling the radiation source, the detector and the reconstruction means,
wherein the reconstruction means obtains the weighting factor according to the correction angle width and the projection data angle for back-projection of the projection data, further obtains the projection data by performing the weighting process based on said weighting factor and assigning the weight to said projection data, and reconstructs a tomogram using the weighted projection data.

16. The tomograph according to claim 15, wherein the imaging controlling means takes images by widening the projection data angle for back-projection and improving SNR.

17. The tomograph according to claim 15, wherein the imaging controlling means takes images by narrowing the projection data angle for back-projection and improving the time resolution.

18. The tomograph according to claim 15 including a means for moving an object relative to the radiation source and the detector, wherein the imaging controlling means changes the correction angle width and/or the projection data angle for back-projection according to the moving speed of the object.

19. The tomograph according to claim 15, wherein the detector is a multi-array detector, and the reconstruction means uses the same weighting factor on each row of the detector.

20. The tomograph according to claim 15, wherein the detector is a multi-array detector, and the reconstruction means uses, with regard to at least one row of the detector, a different weighting factor from other rows.

21. The tomograph according to claim 15 further comprising an input means for inputting the information from a user relating to the correction angle width and the projection data angle for back-projection.

* * * * *